US007666640B2

(12) United States Patent
Yokoyama et al.

(10) Patent No.: US 7,666,640 B2
(45) Date of Patent: Feb. 23, 2010

(54) DNA SEQUENCES FOR THE EXPRESSION OF ALLOPROTEINS

(75) Inventors: Shigeyuki Yokoyama, Tokyo (JP); Mikako Shirouzu, Yokohama (JP); Ayako Sakamoto, Miura (JP); Kensaku Sakamoto, Tokyo (JP)

(73) Assignee: Riken Japan Science and Technology Agency of 1-8 (JP)

( * ) Notice: Subject to any disclaimer, the term of this patent is extended or adjusted under 35 U.S.C. 154(b) by 0 days.

(21) Appl. No.: 12/488,136

(22) Filed: Jun. 19, 2009

(65) Prior Publication Data

US 2009/0286311 A1 Nov. 19, 2009

Related U.S. Application Data

(62) Division of application No. 10/532,948, filed as application No. PCT/JP03/14028 on Oct. 31, 2003, now Pat. No. 7,566,555.

(30) Foreign Application Priority Data

Oct. 31, 2002 (JP) .............................. 2002-318846

(51) Int. Cl.
  *C12P 21/06* (2006.01)
  *C12N 9/00* (2006.01)
  *C07K 1/00* (2006.01)
(52) U.S. Cl. ...................... 435/183; 435/199; 435/325; 536/23.2
(58) Field of Classification Search ...................... None
See application file for complete search history.

(56) References Cited

OTHER PUBLICATIONS

Sakamoto et al., "Site-specific incorporation of an unnatural amino acid into proteins in mammalian cells", Nucleic Acids Research, Nov. 2002, vol. 30, No. 21, 4692-4699.
Supplementary European Search Report dated Nov. 2, 2005.
Wang, Lei, et al., "Expanding the Genetic Code of *Escherichia coli*", *Science*, 292:498-500 (2001).
Kowal, A.K., et al., "Twenty-first aminoacyl-tRNA synthetase-suppressor tRNA pairs for possible use in site-specific incorporation of amino acid analogues into proteins in eukaryotes and in eubacteria" *Proceedings of the National Academy of Science*, 98(5):2268-2273 (2001).
Koide, H., et al., "Biosynthesis of a protein containing a nonprotein amino acid by *Escherichia coli*: L-2-Aminohexanoic acid at position 21 in human epidermal growth factor", *Proceedings of the National Academy of Science*, 85:6237-6241 (1988).
Noren, C.J., et al., "A General Method for Site-Specific Incorporation of Unnatural Amino Acids into Proteins", *Science*, 244:182-188 (1989).
Wang, Lei, et al., "Adding L-3-(2-Naphthyl)alanine to the Genetic Code of *E. coli*", *J. A<. Chem. Soc.*, 124(9):1836-1837 (2002).
Kiga, D., et al., "An engineered *Escherichia coli* tyrosyl-tRNA synthetase for site-specific incorporation of an unnatural amino acid into proteins in eukaryotic translation and its application in a wheat germ cell-free system", *Proceedings of the National Academy of Science*, Jul. 23, 2002, vol. 99, No. 15, p. 9715-9720.
English translation of the article: Kiga, D., et al., "Site-Specific Introduction of 3-Iodotyrosine into Protein in an Cell-Free Translation System of an Eukaryote Using a Mutant Tyrosil-tRNA Synthetase of *Escherichia coli*", *Seikagaku (Biochemistry)*, Aug. 25, 2002, vol. 74, No. 8, p. 1011.
International Search Report for PCT/JP03/14028 dated Jan. 30, 2004.
Wawrousek EF et al., Two large clusters with thirty-seven transfer RNA genes adjacent to ribosomal RNA gene sets in *Bacillus subtilis*. Sequence and organization of trrnD and trrnE gene clusters., J.Biol. Chem., 1984, vol. 259, No. 6, p. 3694-3702.
T. Dingerman et al., "RNA polymerase III catalysed transcription can be regulated in *Saccharomyces cerevisiae* by the bacterial tetracycline repressor-operator system", EMBO J. Apr. 1992, 11 (4), p. 1487-1492.
T. Dingerman et al., "Establishment of a system for conditional gene expression using an inducible tRNA suppressor gene", Mol. Cell. Biol., Sep. 1992, 12(9), p. 4038-4045.
H. Bedouelle, "Recognition of tRNA(Tyr) by tyrosyl-tRNA synthetase", Biochimie, Aug. 1990, 72(8), p. 589-598.
H. van Tol, "A human and a plant intron-containing tRNATyr gener are both transcribed in a HeLa cell extract but spliced along different pathways", EMBO J. Jan. 1987, 6(1), p. 35-41.
M. Sprinzl et al., "Compilation of tRNA sequences and sequences of tTNA genes", Nucleic Acids Research, 1987, 17, r1-r172.

*Primary Examiner*—Andrew Wang
*Assistant Examiner*—Kagnew H Gebreyesus
(74) *Attorney, Agent, or Firm*—Ostrolenk Faber LLP

(57) ABSTRACT

The present invention discloses an expression method for non-naturally-occurring amino acid-containing protein comprising: expressing in animal cells: (A) a mutant tyrosyl-tRNA synthetase that is a mutation of tyrosyl-tRNA synthetase originating in *E. coli* with an enhanced specificity for a non-naturally-occurring tyrosine derivative as compared with the specificity for tyrosine; (B) suppressor tRNA originating in *Bacillus* species, *Mycoplasma* species or *Staphylococcus* species of eubacteria and capable of binding with the tyrosine derivative in the presence of the mutant tyrosyl tRNA synthetase; and, (C) a desired protein gene that has undergone a nonsense mutation at a desired site; wherein, the tyrosine derivative is incorporated at the location of this nonsense mutation.

3 Claims, 8 Drawing Sheets

FIG. 7

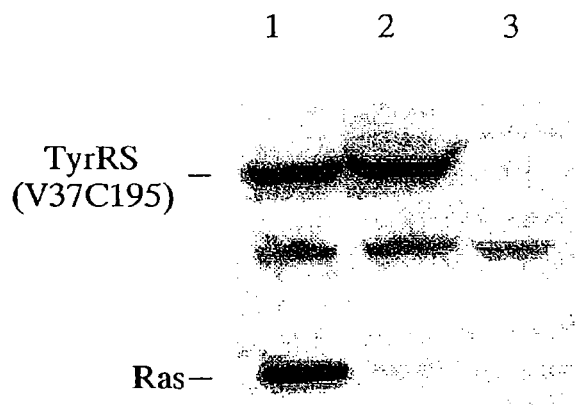

FIG. 8

| | | | |
|---|---|---|---|
| MASSNLIKQL | QERGLVAQVT | DEEALAERLA | 30 |
| QGPIAL<u>Y</u>CGF | DPTADSLHLG | HLVPLLCLKR | 60 |
| FQQAGHKPVA | LVGGATGLIG | DPSFKAAERK | 90 |
| LNTEETVQEW | VDKIRKQVAP | FLDFDCGENS | 120 |
| AIAANNYDWF | GNMNVLTFLR | DIGKHFSVNQ | 150 |
| MINKEAVKQR | LNREDQGISF | TEFSYNLLQG | 180 |
| YDFACLNKQY | GVVL<u>Q</u>IGGSD | QWGNITSGID | 210 |
| LTRRLHQNQV | FGLTVPLITK | ADGTKFGKTE | 240 |
| GGAVWLDPKK | TSPYKFYQFW | INTADADVYR | 270 |
| FLKFFTFMSI | EEINALEEED | KNSGKAPRAQ | 300 |
| YVLAEQVTRL | VHGEEGLQAA | KRITECLFSG | 330 |
| SLSALSEADF | EQLAQDGVPM | VEMEKGADLM | 360 |
| QALVDSELQP | SRGQARKTIA | SNAITINGEK | 390 |
| QSDPEYFFKE | EDRLFGRFTL | LRRGKKNYCL | 420 |
| ICWK | | | 424 |

SEQUENCE LISTING

```
<160> NUMBER OF SEQ ID NOS: 32

<210> SEQ ID NO 1
<211> LENGTH: 167
<212> TYPE: DNA
<213> ORGANISM: Artificial
<220> FEATURE:
<223> OTHER INFORMATION: an artificial base sequence consisting of
      a leader sequence of human tRNA gene,and the tRNAtyr gene of B.
      stearothermophilus with a CUA anticodon, but without the terminal
      CCA sequence and a transcription terminator

<400> SEQUENCE: 1
agcgctccgg tttttctgtg ctgaacctca ggggacgccg acacacgtac acgtcggagg    60
```

-continued ggtagcgaag tggctaaacg cggcggactc taaatccgct cccttttgggt tcggcggttc    120 gaatccgtcc ccctccagac aagtgcggtt tttttctcca gctcccg                  167

<210> SEQ ID NO 2
<211> LENGTH: 44
<212> TYPE: DNA
<213> ORGANISM: Artificial
<220> FEATURE:
<223> OTHER INFORMATION: a PCR primer used for amplifying a part of
      genomic DNA of E. coli

<400> SEQUENCE: 2
ggaattccat atggcaagca gtaacttgat taaacaattg caag                      44

<210> SEQ ID NO 3
<211> LENGTH: 50
<212> TYPE: DNA
<213> ORGANISM: Artificial
<220> FEATURE:
<223> OTHER INFORMATION: a PCR primer used for amplifying a part of
      genomic DNA of E. coli.

<400> SEQUENCE: 3
gccgaagctt gtcgactttc cagcaaatca gacagtaatt cttttttaccg               50

<210> SEQ ID NO 4
<211> LENGTH: 40
<212> TYPE: DNA
<213> ORGANISM: Artificial
<220> FEATURE:
<223> OTHER INFORMATION: a PCR primer used in the overlapping
      extension in the present invention

<400> SEQUENCE: 4
aggatcgaag ccgcaagcga gcgcgatcgg gccttgcgcc                           40

<210> SEQ ID NO 5
<211> LENGTH: 40
<212> TYPE: DNA
<213> ORGANISM: Artificial
<220> FEATURE:
<223> OTHER INFORMATION: a PCR primer used in the overlapping extension
      in the present invention
<220> FEATURE:
<221> NAME/KEY: misc_feature
<222> LOCATION: (16)..(16)
<223> OTHER INFORMATION: m represents c or a
<220> FEATURE:
<221> NAME/KEY: misc_feature
<222> LOCATION: (17)..(18)
<223> OTHER INFORMATION: n is a, c, g, or t

<400> SEQUENCE: 5
aggatcgaag ccgcamnnga gcgcgatcgg gccttgcgcc                           40

<210> SEQ ID NO 6
<211> LENGTH: 33
<212> TYPE: DNA
<213> ORGANISM: Artificial
<220> FEATURE:
<223> OTHER INFORMATION: a PCR primer used in the overlapping
      extension in the present invention

<400> SEQUENCE: 6
acggtgtggt gctgtctatt ggtggttctg acc                                  33

```
<210> SEQ ID NO 7
<211> LENGTH: 33
<212> TYPE: DNA
<213> ORGANISM: Artificial
<220> FEATURE:
<223> OTHER INFORMATION: a PCR primer used in the overlapping extension
      in the present invention

<400> SEQUENCE: 7
acggtgtggt gctggcaatt ggtggttctg acc                                    33

<210> SEQ ID NO 8
<211> LENGTH: 33
<212> TYPE: DNA
<213> ORGANISM: Artificial
<220> FEATURE:
<223> OTHER INFORMATION: a PCR primer used in the overlapping
      extension in the present invention

<400> SEQUENCE: 8
acggtgtggt gctgaacatt ggtggttctg acc                                    33

<210> SEQ ID NO 9
<211> LENGTH: 33
<212> TYPE: DNA
<213> ORGANISM: Artificial
<220> FEATURE:
<223> OTHER INFORMATION: a PCR primer used in the overlapping
      extension in the present invention

<400> SEQUENCE: 9
acggtgtggt gctgtgcatt ggtggttctg acc                                    33

<210> SEQ ID NO 10
<211> LENGTH: 32
<212> TYPE: DNA
<213> ORGANISM: Artificial
<220> FEATURE:
<223> OTHER INFORMATION: a PCR primer used in the overlapping
      extension in the present invention

<400> SEQUENCE: 10
ttcttcggat ccaaccagac tgcgccgcct tc                                     32

<210> SEQ ID NO 11
<211> LENGTH: 30
<212> TYPE: DNA
<213> ORGANISM: Artificial
<220> FEATURE:
<223> OTHER INFORMATION: a PCR primer used in the overlapping
      extension in the present invention

<400> SEQUENCE: 11
gatcatctgg ttaacggaga agtgtttgcc                                        30

<210> SEQ ID NO 12
<211> LENGTH: 26
<212> TYPE: DNA
<213> ORGANISM: Artificial
<220> FEATURE:
<223> OTHER INFORMATION: a PCR primer used in the overlapping
      extension in the present invention

<400> SEQUENCE: 12
gaccttcctg tgcgatattg gcaaac                                            26

<210> SEQ ID NO 13
```

```
<211> LENGTH: 12
<212> TYPE: DNA
<213> ORGANISM: Artificial
<220> FEATURE:
<223> OTHER INFORMATION: the box A consensus sequence
<220> FEATURE:
<221> NAME/KEY: misc_feature
<222> LOCATION: (2)..(2)
<223> OTHER INFORMATION: r represents g or a
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 13
trgcnnagyn gg                                                         12

<210> SEQ ID NO 14
<211> LENGTH: 11
<212> TYPE: DNA
<213> ORGANISM: Artificial
<220> FEATURE:
<223> OTHER INFORMATION: the box B consensus sequence
<220> FEATURE:
<221> NAME/KEY: misc_feature
<222> LOCATION: (8)..(8)
<223> OTHER INFORMATION: n is a, c, g, or t

<400> SEQUENCE: 14
ggttcgantc c                                                          11

<210> SEQ ID NO 15
<211> LENGTH: 20
<212> TYPE: DNA
<213> ORGANISM: Artificial
<220> FEATURE:
<223> OTHER INFORMATION: a sequence of a primer binding site pbs1

<400> SEQUENCE: 15
agcgagtgtt aaccctgcct                                                 20

<210> SEQ ID NO 16
<211> LENGTH: 20
<212> TYPE: DNA
<213> ORGANISM: Artificial
<220> FEATURE:
<223> OTHER INFORMATION: a sequence of a primer binding site pbs2

<400> SEQUENCE: 16
cgactacgat attcgcgcag                                                 20

<210> SEQ ID NO 17
<211> LENGTH: 12
<212> TYPE: DNA
<213> ORGANISM: Artificial
<220> FEATURE:
<223> OTHER INFORMATION: a sequence of a BstXI-1 site

<400> SEQUENCE: 17
ccagcagact gg                                                         12

<210> SEQ ID NO 18
<211> LENGTH: 12
<212> TYPE: DNA
<213> ORGANISM: Artificial
```

```
<220> FEATURE:
<223> OTHER INFORMATION: a sequence of a BstXI-2 site

<400> SEQUENCE: 18
ccagcttcct gg                                                            12

<210> SEQ ID NO 19
<211> LENGTH: 63
<212> TYPE: DNA
<213> ORGANISM: Artificial
<220> FEATURE:
<223> OTHER INFORMATION: a nucleotide sequence coding a short
      peptide used for substitution of green fluorescent protein
      (cyanfluorescent mutation)

<400> SEQUENCE: 19
atgggaacta gtccatagtg gtggaattct gcagatatcc agcacagtgg cggccgccgc        60
gtc                                                                      63

<210> SEQ ID NO 20
<211> LENGTH: 11
<212> TYPE: DNA
<213> ORGANISM: Artificial
<220> FEATURE:
<223> OTHER INFORMATION: another box B consensus sequence
<220> FEATURE:
<221> NAME/KEY: misc_feature
<222> LOCATION: (8)..(8)
<223> OTHER INFORMATION: n is a, c, g, or t

<400> SEQUENCE: 20
agttcgantc t                                                             11

<210> SEQ ID NO 21
<211> LENGTH: 31
<212> TYPE: DNA
<213> ORGANISM: Artificial
<220> FEATURE:
<223> OTHER INFORMATION: a sequence of a primer used for amplifying the
      sequence of SEQ ID No. 1

<400> SEQUENCE: 21
cacagaattc tcgggagctg gagaaaaaaa c                                       31

<210> SEQ ID NO 22
<211> LENGTH: 30
<212> TYPE: DNA
<213> ORGANISM: Artificial
<220> FEATURE:
<223> OTHER INFORMATION: a sequence of another primer used for
      amplifying the sequence of SEQ ID No. 1

<400> SEQUENCE: 22
cacaaagctt agcgctccgg tttttctgtg                                         30

<210> SEQ ID NO 23
<211> LENGTH: 40
<212> TYPE: DNA
<213> ORGANISM: Artificial
<220> FEATURE:
<223> OTHER INFORMATION: a sequence of a primer set used for
      amplifying a fragment having a primer binding site pbs1 upstream
      of the sequence of SEQ ID No. 1 and BstXI-1 site downstream
      thereof

<400> SEQUENCE: 23
agcgagtgtt aaccctgcct agcgctccgg tttttctgtg                              40
```

-continued

<210> SEQ ID NO 24
<211> LENGTH: 38
<212> TYPE: DNA
<213> ORGANISM: Artificial
<220> FEATURE:
<223> OTHER INFORMATION: a sequence of a primer set used for
      amplifying a fragment having a primer binding site pbs1 upstream
      of the sequence of SEQ ID No. 1 and BstXI-1 site downstream
      thereof

<400> SEQUENCE: 24
acacacccag cagactggcg ggagctggag aaaaaaac                            38

<210> SEQ ID NO 25
<211> LENGTH: 38
<212> TYPE: DNA
<213> ORGANISM: Artificial
<220> FEATURE:
<223> OTHER INFORMATION: a sequence of a primer set used for
      amplifying a fragment having a BstXI-1 site upstream of the
      sequence of SEQ ID No. 1 and another BstXI-1 site downstream
      from the first BstXI-1 site

<400> SEQUENCE: 25
acacacccag cagactggag cgctccggtt tttctgtg                            38

<210> SEQ ID NO 26
<211> LENGTH: 38
<212> TYPE: DNA
<213> ORGANISM: Artificial
<220> FEATURE:
<223> OTHER INFORMATION: a sequence of a primer set used for amplifying
      a fragment having a BstXI-1 site upstream of the sequence of
      SEQ ID No. 1 and another BstXI-1 site downstream from the first
      BstXI-1 site

<400> SEQUENCE: 26
acacacccag cttcctggcg ggagctggag aaaaaaac                            38

<210> SEQ ID NO 27
<211> LENGTH: 38
<212> TYPE: DNA
<213> ORGANISM: Artificial
<220> FEATURE:
<223> OTHER INFORMATION: a sequence of a primer set used for amplifying
      a fragment having a BstXI-2 site upstream of the sequence of
      SEQ ID No. 1 and a primer binding site pbs-2

<400> SEQUENCE: 27
acacacccag cttcctggag cgctccggtt tttctgtg                            38

<210> SEQ ID NO 28
<211> LENGTH: 40
<212> TYPE: DNA
<213> ORGANISM: Artificial
<220> FEATURE:
<223> OTHER INFORMATION: a sequence of a primer set used for amplifying
      a fragment hving a BstXI-2 site upstream of the sequence of
      SEQ ID No. 1 and a primer binding site pbs-2

<400> SEQUENCE: 28
ctgcgcgaat atcgtagtcg cgggagctgg agaaaaaaac                          40

<210> SEQ ID NO 29
<211> LENGTH: 424
<212> TYPE: PRT
<213> ORGANISM: Escherichia coli -continued

<400> SEQUENCE: 29

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Tyr Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Asp Phe Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
```

```
                  405                 410                 415
Asn Tyr Cys Leu Ile Cys Trp Lys
            420

<210> SEQ ID NO 30
<211> LENGTH: 135
<212> TYPE: DNA
<213> ORGANISM: Artificial
<220> FEATURE:
<223> OTHER INFORMATION: a sequence of one of the induced expression
      systems prepared in Example 2 (TetBst0)

<400> SEQUENCE: 30
tctccctatc agtgatagag atcggagggg tagcgaagtg gctaaacgcg gcggactcta        60
aatccgctcc ctttgggttc ggcggttcga atccgtcccc ctccagacaa gtgcggtttt       120
tttctccagc tcccg                                                        135

<210> SEQ ID NO 31
<211> LENGTH: 145
<212> TYPE: DNA
<213> ORGANISM: Artificial
<220> FEATURE:
<223> OTHER INFORMATION: a sequence of one of the induced expression
      systems prepared in Example 1 (TetBst1)

<400> SEQUENCE: 31
tctccctatc agtgatagag atccgtacac gtcggagggg tagcgaagtg gctaaacgcg        60
gcggactcta aatccgctcc ctttgggttc ggcggttcga atccgtcccc ctccagacaa       120
gtgcggtttt tttctccagc tcccg                                             145

<210> SEQ ID NO 32
<211> LENGTH: 155
<212> TYPE: DNA
<213> ORGANISM: Artificial
<220> FEATURE:
<223> OTHER INFORMATION: a sequence of one of the induced expression
      systems prepared in Example 2 (TetBst2)

<400> SEQUENCE: 32
tctccctatc agtgatagag atccgccgac acacgtacac gtcggagggg tagcgaagtg        60
gctaaacgcg gcggactcta aatccgctcc ctttgggttc ggcggttcga atccgtcccc       120
ctccagacaa gtgcggtttt tttctccagc tcccg                                  155
```

DNA SEQUENCES FOR THE EXPRESSION OF ALLOPROTEINS

CROSS REFERENCE TO RELATED APPLICATION

This application which is a divisional application of U.S. application Ser. No. 10/532,948 filed on Jan. 9, 2006, now U.S. Pat. No. 7,566,555 which is a 35 U.S.C. §371 national phase conversion of PCT/JP2003/014028 filed 31 Oct. 2003, which claims priority to Japanese Application No. 2002-318846 filed on 31 Oct. 2002.

The PCT International Application was published in the Japanese language.

BACKGROUND OF THE INVENTION

1. Field of the Invention

The present invention relates to a non-naturally-occurring amino acid-incorporated protein expression method by which a non-naturally occurring amino acid is incorporated at a desired site in a protein, as well as DNA, an expression vector and animal cells used for expressing the aforementioned protein.

2. Description of the Related Art

Non-naturally-occurring amino acid-containing proteins (to also be referred to as alloproteins), in which an amino acid residue at a desired location in a protein is substituted with an amino acid other than the 20 types of amino acids normally involved in protein synthesis (to be referred to as non-naturally-occurring amino acids), offer an effective means of analyzing the function and structure of proteins.

Aminoacyl t-RNA synthetases (to be referred to as aaRS) are enzymes that specifically bind amino acids and tRNA, and excluding a few exceptions, there are 20 types of such enzymes corresponding to each of the 20 types of amino acids that exist in nature for each biological species. Since these aaRS are basically present for each amino acid within cells, the type of amino acid assigned to the genetic code is determined. For example, TyrRS, which is a kind of aaRS (to simply be referred to as TyrRS), distinguishes tyrosine tRNA (to be referred to as tRNA$^{Tyr}$) from the tRNA of other amino acids, and binds only tyrosine to tRNA$^{Tyr}$ without binding other amino acids.

Known methods for producing alloproteins in the prior art consist of a method that produces alloproteins in *Escherichia coli* (Koide, et al., Proceedings of the National Academy of Science USA, Vol. 85, 1988, pp. 6237-6241 (Document 1)), and a method that produces alloproteins in a cell-free translation system (Noren, et al., Science, Vol. 244, 1989, pp. 182-188 (Document 2)).

In order to prepare proteins containing 21 types of amino acids, including non-naturally-occurring amino acids, in large yield, it is necessary to construct an artificial genetic code system by which tRNAs are aminoacylated with non-naturally-occurring amino acids by specific aaRSs in a system in which a translation reaction takes place.

It is necessary to find aaRS-tRNA pairs that satisfy the following conditions in order to construct such an artificial genetic code system:

(1) the aaRS must be an aaRS mutant that reacts specifically with a desired non-naturally occurring amino acid and not with any of the ordinary 20 types of amino acids; and, (2) the tRNA must be assigned to a codon to which none of the ordinary 20 types of amino acids are assigned (such as a nonsense codon or 4-base codon), must be recognized only by the aforementioned aaRS mutant specific for a non-naturally-occurring amino acid, and must not be recognized by any aaRS of the host (orthogonal tRNA).

A tRNA molecule that binds a non-naturally-occurring amino acid and transport it to a nonsense codon on messenger RNA (suppressor tRNA molecule), and an enzyme that binds a non-naturally-occurring amino acid to this suppressor tRNA molecule (aaRs), can be used to create a genetic code system that satisfies these conditions. This mechanism is described in Wang, et al., Science, Vol. 292, 2001, pp. 498-500 (Document 3) and Journal of the American Chemical Society, Vol. 124, 2002, pp. 1836-1937 (Document 4).

Specific artificial genetic code systems based on this mechanism have been established in *E. coli* as well as cell-free protein synthesis systems using wheat germ extract.

Namely, a system for producing protein containing a non-naturally-occurring amino acid at an arbitrary specified site in *E. coli* has been reported that consists of O-methyltyrosine being specifically inserted corresponding to an amber codon by expressing a TyrRS mutant originating in *Methanococcus jannaschii* that has been altered so as to specifically aminoacylate O-methyltyrosine, and an amber suppressor tRNA in which tyrosine tRNA from the same microorganism has been altered (Document 3).

In addition, aaRS has been developed for producing protein containing a non-naturally-occurring amino acid at an arbitrary site in wheat germ extract (Kiga, et al., Proceedings of the National Academy of Science USA, Vol. 99, Jul. 23, 2002, pp. 9715-9723 (Document 5)).

In this manner, although alloprotein production systems have been developed in *E. coli* and cell-free protein synthesis systems, these cannot be used directly in animal cells. Namely, these molecules developed for use in *E. coli* cannot be used in animal cells due the properties of the molecules themselves. In order to synthesize protein containing a non-naturally-occurring amino acid at an arbitrary specified site in animal cells, suitable suppressor tRNA and aaRS specific for both this suppressor tRNA and the non-naturally-occurring amino acid must be developed, and the expression of those molecules must be realized in animal cells.

In addition, the aforementioned aaRS used in a cell-free protein synthesis system in wheat germ extract is predicted to be able to be used in animal cells in consideration of its substrate specificity. However, in order to use this aaRS, it is necessary to develop suppressor tRNA to be combined therewith along with the expression system for this tRNA.

SUMMARY OF THE INVENTION

The object of the present invention is to provide a method for expressing non-naturally-occurring amino acid-containing protein in animal cells, and to provide DNA, an expression vector and animal cells for expressing that protein.

The present invention provides the expression methods described below.

(1) An expression method for non-naturally-occurring amino acid-containing protein comprising: expressing in animal cells:

(A) a mutant TyrRS that is a derivative of TyrRS originating from *E. coli* with an enhanced specificity for a non-naturally-occurring tyrosine derivative as compared with the specificity for tyrosine (referred to as mutant TyrRS);

(B) suppressor tRNA originating in *Bacillus* species, *Mycoplasma* species or *Staphylococcus* species of eubacteria and capable of binding with the tyrosine derivative in the presence of the mutant TyrRS; and, (C) a desired protein gene that has undergone a nonsense mutation at a desired site;

wherein, the tyrosine derivative is incorporated in response to the created nonsense codon.

(2) The expression method according to (1) wherein the tyrosine derivative is a position 3-substituted tyrosine or position 4-substituted tyrosine.

(3) The expression method according to (1) or (2) wherein the suppressor tRNA of (B) is suppressor tRNA$^{Tyr}$ originating in *Bacillus stearothermophilus*.

(4) The expression method according to any of (1) to (3) wherein the mutant TyrRS of (A) is a mutant TyrRS that has undergone an alteration at the location corresponding to tyrosine at position 37 and glutamine at position 195 of TyrRS.

(5) The expression method according to (4) wherein the mutant TyrRS of (A) is a mutant TyrRS in which the location corresponding to tyrosine (Y) at position 37 of TyrRS is substituted with valine (V), leucine (L), isoleucine (I) or alanine (A), and the location corresponding to glutamine (Q) at position 195 of TyrRS is substituted with alanine (A), cysteine (C), serine (S) or asparagine (N).

(6) The expression method according to any of (1) to (5) wherein the animal cells are mammalian cells.

In addition, the present invention provides the protein production method described below.

(7) A non-naturally-occurring amino acid-containing protein production method comprising: recovering and purifying a protein expressed according to any of the methods described in (1) to (6).

In addition, the present invention also provides the animal cells described below.

(8) Animal cells containing:

(A) an expression vector that expresses in animal cells a mutant of TyrRS from *E. coli* with an enhanced specificity for a non-naturally-occurring tyrosine derivative as compared with the specificity for tyrosine;

(B) an expression vector that expresses in the animal cells a suppressor tRNA originating in a *Bacillus* species, *Mycoplasma* species or *Staphylococcus* species of eubacteria capable of binding with the tyrosine derivative in the presence of the mutant TyrRS; and, (C) an expression vector that expresses in the animal cells a desired protein gene that has undergone a nonsense mutation at a desired site; wherein, the tyrosine derivative is incorporated at the site of the nonsense mutation of the protein.

(9) The animal cells according to (8) wherein the tyrosine derivative is a position 3-substituted tyrosine or position 4-substituted tyrosine.

(10) The animal cells according to (8) or (9) wherein the suppressor tRNA of (B) is suppressor tRNA$^{Tyr}$ originating in *Bacillus stearothermophilus*.

(11) The animal cells according to any of (8) to (10) wherein the mutant TyrRS of (A) is a mutant TyrRS that has undergone an alteration at the location corresponding to tyrosine at position 37 and glutamine at position 195 of TyrRS.

(12) The animal cells according to (11) wherein the mutant TyrRS of (A) is a mutant TyrRS in which the location corresponding to tyrosine (Y) at position 37 of TyrRS is substituted with valine (V), leucine (L), isoleucine (I) or alanine (A), and the location corresponding to glutamine (Q) at position 195 of TyrRS is substituted with alanine (A), cysteine (C), serine (S) or asparagine (N).

(13) The animal cells according to any of (8) through (12) that are mammalian cells.

In addition, the present invention provides the DNA and expression vectors described below.

(14) DNA having a sequence selected from the group consisting of SEQ. ID NO. 1, SEQ. ID NO. 30, SEQ. ID NO. 31 and SEQ. ID NO. 32.

(15) An expression vector capable of being expressed from a control sequence recognized in animal cells comprising a sequence selected from the group consisting of SEQ. ID NO. 1, SEQ. ID NO. 30, SEQ. ID NO. 31 and SEQ. ID NO. 32.

(16) The expression vector according to (15) that carries nine copies DNA having the sequence of SEQ. ID NO. 1 in the same direction.

BRIEF DESCRIPTION OF THE DRAWINGS

In FIG. 2, s$^4$U indicates 4-thiouridine, Gm indicates 2'-O-methylguanosine, ms$^2$t$^6$A indicates 2-methyl-thio-N$^6$-isopentyladenosine, T indicates 5-methyluridine, Ψ indicates pseudouridine and m$^1$A indicates 1-methyladenosine.

FIG. 7 is a photograph of a western blot of inducible amber suppression for the incorporation of 3-iodo-L-tyrosine into Ras protein.

FIG. 8 is a drawing showing an amino acid sequence (one-letter sequence code) of TyrRS (wild type) of *E. coli* (SEQ ID NO: 29).

DETAILED DESCRIPTION OF THE PREFERRED EMBODIMENTS

Figure 1:
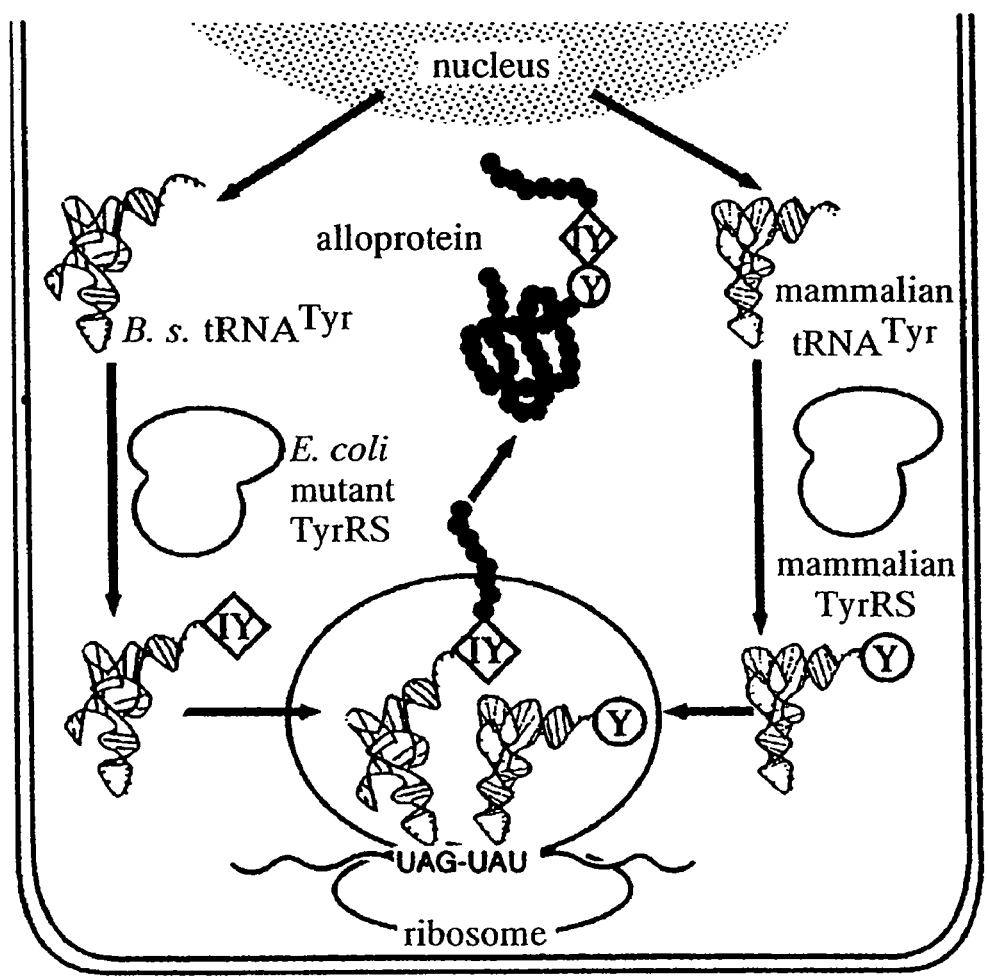
FIG. 1 is an explanatory drawing showing a mammalian cell system for incorporating 3-iodo-L-tyrosine in response to an amber codon into a protein gene. Although the 3-iodo-L-tyrosine (IY) is also present with L-tyrosine (Y) in the medium, it binds to any B.s. tRNA$^{Tyr}$ (*Bacillus stearothermophilus* tRNA$^{Tyr}$) due to a specific *E. coli* TyrRS introduced into the cells.

The expression method of the present invention is:

an expression method for non-naturally-occurring amino acid-containing protein comprising: expressing in animal cells:

(A) a mutant TyrRS that is a derivative of TyrRS originating in prokaryote with an enhanced specificity for a non-naturally-occurring tyrosine derivative as compared with specificity for tyrosine;

(B) suppressor tRNA originating in *Bacillus* species, *Mycoplasma* species or *Staphylococcus* species of eubacteria and capable of binding with the tyrosine derivative in the presence of the mutant TyrRS; and, (C) a desired protein gene that has undergone a nonsense mutation at a desired site;

wherein, the tyrosine derivative is incorporated at the location of the protein nonsense mutation.

Next, a detailed description is provided of the mutant TyrRS and suppressor tRNA used in the expression method of the present invention.

(1) Mutant TyrRS

In the present invention, enhanced substrate affinity for a desired tyrosine derivative as compared with tyrosine means that the activity value (value obtained by dividing the reaction rate $K_{cat}$ by the Michealis constant $K_m$) for the target tyrosine derivative is greater than the activity value for tyrosine. Although the activity value can be measured by an in vitro assay, the relative magnitude of an activity value can also be determined from genetic data.

The mutant TyrRS used in the present invention is a derivative of TyrRS form *E. coli* that specifically recognizes a tyrosine derivative, specifically recognizes suppressor tRNA used in combination therewith and forms the suppressor tRNA aminoacylated with the tyrosine derivative. Examples of *E. coli* include strain K12 and strain B.

The TyrRS (wild type) originating in *E. coli* does not react with $tRNA^{Tyr}$ of eukaryotes, while $tRNA^{Tyr}$ originating in *E. coli* does not react with TyrRS of eukaryotes.

Examples of the aforementioned tyrosine derivative include position 3-substituted tyrosine and position 4-substituted tyrosine having a substituent at position 3 or position 4 of the phenyl group of tyrosine.

Examples of position 3-substituted tyrosine include 3-halogenated tyrosines such as 3-iodotyrosine and 3-bromotyrosine. In addition, examples of position 4-substituted tyrosine include 4-acetyl-L-phenylalanine, 4-benzoyl-L-phenylalanine, 4-azido-L-phenylalanine, O-methyl-L-tyrosine and 4-iodo-L-phenylalanine.

These amino acids can be produced with known methods or commercially available amino acids can be used. For example, 4-acetyl-L-phenylalanine can be produced according to the method described in Biochemistry, Vol. 42, pp. 6735-6746, 2003. In addition, commercially available products obtained from Bachem (Germany) can be used for 4-benzoyl-L-phenylalanine and 4-azido-L-phenylalamine, and commercially available products obtained from Sigma (USA) can be used for O-methyl-L-tyrosine and 4-iodo-L-phenylalanine.

These amino acids themselves are non-naturally-occurring amino acids having physiological activity, or to be used as targets of site-specific labels of proteins. Therefore, a protein containing a 3-halogenated tyrosine, for example, is useful as a research material for analyzing the structure and function of this protein, while proteins containing other amino acids may have the potential for being a target of drug development.

The amino acid sequence (SEQ. ID NO. 29) of TyrRS (wild type) of *E. coli* is shown in FIG. 8 using a one-letter symbols for amino acids.

The gene coding for the mutant TyrRS used in the present invention can be prepared by substituting the amino acid residues probably involved in the recognition of tyrosyl-AMP by the enzyme, by a known method of site-directed mutagenesis (described later). These amino acids are identified in the sequence shown in FIG. 8 by referring to the amino acids involved in the tyrosyl-AMP recognition in a known tertiary structure of the complex between TyrRS and tyrosyl-AMP (for example, Brick et al., J. Mol. Biol. Vol. 208, p. 83, 1988).

A preferable example of a mutant TyrRS used in the present invention is a mutant on which specificity for 3-halogenated tyrosine is conferred by site-specifically substituting at least the locations corresponding to tyrosine (Y) at position 37 and glutamine (Q) at position 195 with other amino acids in this sequence (see Document 5).

More preferably, a mutant TyrRS can be used in which the location corresponding to tyrosine (Y) at position 37 is substituted with valine (V), leucine (L), isoleucine (I) or alanine (A), and the location corresponding to glutamine (Q) at position 195 is substituted with alanine (A), cysteine (C), serine (S) or asparagine (N). Results demonstrating that the specificity for 3-halogenated tyrosines is enhanced by these mutations are shown in Table 1. Table 1 shows the measurement of an aminoacylation reaction by detecting inorganic phosphorous using Biomol Green (Funakoshi) based on a simplified version of the method of Lloyd, et al. that quantifies the amount of inorganic phosphoric acid produced by degrading pyrophosphoric acid, which is one of the reaction products of the aminoacylation reaction, with pyrophosphatase (Lloyd, et al., Nucleic Acids Research, Vol. (1995) pp. 2286-2892).

TABLE 1

Activity of TyrRS variants with tyrosine, 3-iodo-L-tyrosine

| Enzyme | Amino acid | | Enzyme | Amino acid | |
| --- | --- | --- | --- | --- | --- |
| | Tyrosine | 3-iodo-L-tyrosine | | Tyrosine | 3-iodo-L-tyrosine |
| Wild Type (Y37, Q195) | +++ | − | V37 | +++ | +++ |
| A37A195 | − | − | I37A195 | + | + |
| A37C195 | + | ++ | I37C195 | − | − |
| A37N195 | − | − | I37N195 | − | − |
| A37S195 | + | + | I37S195 | − | − |
| V37A195 | + | ++ | L37A195 | + | − |
| V37C195 | + | ++ | L37C195 | + | + |
| V37N195 | + | ++ | L37N195 | + | − |
| V37S195 | ++ | ++ | L37S195 | − | − |

+++: the activity detected with an enzyme concentration of 0.05 µM
++: the activity detected with an enzyme concentration of 0.25 µM
+: the activity detected with an enzyme concentration of 0.25 µM, although the activity is lower than that represented by "++"
−: no activity detected with an enzyme concentration of 0.25 µM In particular, based on the results of Table 1, the mutant in which position 37 is valine and position 195 is cysteine (to be referred to as V37C195), the mutant in which position 37 is valine and position 195 is asparagine (referred to as V37N195), the mutant in which position 37 is valine and position 195 is alanine (referred to as V37A195) and the mutant in which position 37 is alanine and position 195 is cysteine (referred to as A37C195) are particularly preferable.

Next, a method using a known genetic manipulation technique is preferable for the method used to produce these mutants. For example, DNA sequences with desired amino acid replacements are amplified with the primers for achieving these replacements, and are then concatenated with each other into the full-length gene for a desired mutant aaRS. This aaRS may easily be prepared by expressing it in host cells, such as *E. coli*. The primer used in this method has 20 to 70 bases and preferably about 20 to 50 bases. Since this primer is mismatched by 1 to 3 bases with the original base sequence prior to alteration, the use of a comparatively long primer of, for example, 20 bases or more is preferable.

More specifically, the fragment amplified by PCR according to the method described in Document 5 using the following primers (1) and (2), together with *E. coli* genomic DNA for the PCR template, are treated with NdeI and HindIII, followed by the incorporation of this fragment at the NdeI-HindIII site of pET26b to produce TyrRS expression vector pRT-YRS. The use of *E. coli* genomic DNA for the template means that *E. coli* cells collected from about 0.1 mL of *E. coli* culture are heated for 10 minutes at 95° C. before being added to the PCR reaction mixture.

Primer (1):
(SEQ. ID NO. 2)
GGAATTCCATATGGCAAGCAGTAACTTGATTAAACAATTGCAAG

Primer (2):
(SEQ. ID NO. 3)
GCCGAAGCTTGTCGACTTTCCAGCAAATCAGACAGTAATTCTTTTTACCG

Next, an explanation is provided of an example of a method for site-specifically altering amino acids at positions 37 and 195.

First, mutants are produced in which only one amino acid is substituted at position 37 or position 195. The primers (3) to (8) used to produce DNA sequences that encode mutants in which one amino acid each is substituted at position 37 and position 195 are as shown below.

Primer (3):
(SEQ. ID NO. 4)
AGGATCGAAGCCGCAAGCGAGCGCGATCGGGCCTTGCGCC

Primer (4):
(SEQ. ID NO. 5)
AGGATCGAAGCCGCAMNNGAGCGCGATCGGGCCTTGCGCC

M represents C or A, and N represents A, C, G or T.

Primer (5):
(SEQ. ID NO. 6)
ACGGTGTGGTGCTGTCTATTGGTGGTTCTGACC

Primer (6):
(SEQ. ID NO. 7)
ACGGTGTGGTGCTGGCAATTGGTGGTTCTGACC

Primer (7):
(SEQ. ID NO. 8)
ACGGTGTGGTGCTGAACATTGGTGGTTCTGACC

Primer (8):
(SEQ. ID NO. 9)
ACGGTGTGGTGCTGTGCATTGGTGGTTCTGACC

Next, mutants are created in which the amino acids at positions 37 and 195 are both substituted.

The DNA sequence coding for the mutant with both substitutions is created by an overlap extension using the plasmids carrying the above mutant genes each with a single substitution at position 37 or 195, and is then inserted between the NdeI and BamHI sites of pET-YRS. This overlap extension can be performed by PCR with the primers (1) and (9) for amplifying two DNA fragments partially overlapped with each other. These fragments are obtained by PCR with primer pairs (1) and (10), and (9) and (11) and purified for the use in the overlap extension.

Primer (1):
(SEQ. ID NO. 2)
GGAATTCCATATGGCAAGCAGTAACTTGATTAAACAATTGCAAG

Primer (10):
(SEQ. ID NO. 11)
GATCATCTGGTTAACGGAGAAGTGTTTGCC

Primer (9):
(SEQ. ID NO. 10)
TTCTTCGGATCCAACCAGACTGCGCCGCCTTC

Primer (11):
(SEQ. ID NO. 12)
GACCTTCCTGTGCGATATTGGCAAAC

Each of the full-length mutant DNA fragments obtained in the aforementioned process is inserted into the locations of the template fragments inside plasmid PET-YRS, and inserted into each *E. coli* BLR (DE3) according to a transformation method complying the method of Hanahan (Hanahan, D., J. Mol. Bio., 166, 557-580) with plasmids containing mutant TyrRS gene. Mutant TyrRS can then be expressed in *E. coli* by isolating and culturing transformants having each plasmid.

Moreover, the method used to create mutant TyrRS is not limited to the aforementioned method, but rather various genetic manipulation technologies can be used, including known point mutation technologies and methods for inserting altered fragments using restriction endonuclease.

(2) Suppressor tRNA

Suppressor tRNA used in combination with the aforementioned mutant TyrRS satisfies the requirements of being assigned to a nonsense codon, which is no codon assigned to the normal 20 types of amino acids, being recognized only by the aforementioned non-naturally-occurring amino acid-specific TyrRS mutant, not being recognized by any aaRS of the host, and being able to expressed in eukaryotic cells.

Although all of three nonsense codons UAG (amber), UAA (ochre) and UGA (opal) are usable, UAG (amber) is used preferably.

The inventors of the present invention checked whether suppressor tRNA originating in *E. coli* would be suitable for being combined with mutant TyrRS originating in *E. coli*, and tried to express this *E. coli* suppressor tRNA$^{Tyr}$ in eukaryotic cells. The sequence and structure of suppressor tRNA$^{Tyr}$ originating in *E. Coli* tRNA$^{Tyr}$ are already known (M. Sprinzl, et al., Nucleic Acids Research, 17, 1-172 (1989)). This is shown in FIG. 2.

In general, the expression of tRNA in eukaryotic cells requires two internal promoters within the tRNA coding sequence, and their consensus sequences are known as box A and box B. The consensus sequence of box A (TRGCN-NAGYNGG; SEQ. ID NO. 13) corresponds to TRGCN-NAGY at positions 8 to 16 and GG at positions 18 and 19 of tRNA, while the consensus sequence of box B corresponds to GGTTCGANTCC at positions 52 to 62 (SEQ. ID NO. 14). These positions are encircled in FIG. 2. The consensus sequence of box B may also be AGTTCGANTCT (SEQ. ID NO. 20).

Figure 2:
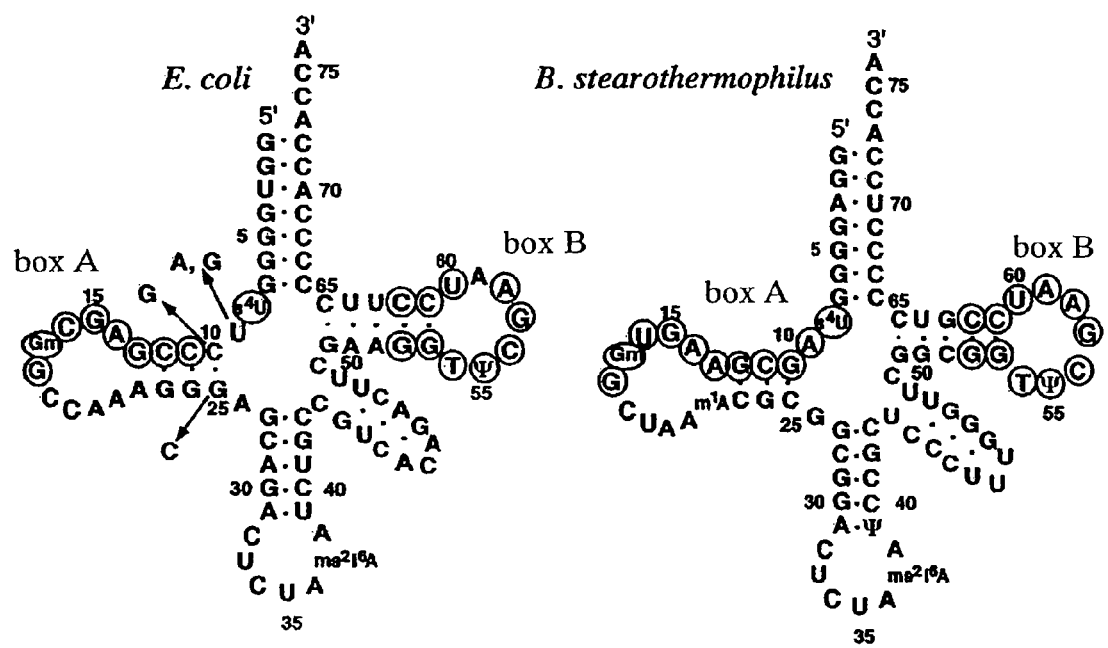
FIG. 2 shows the sequence and structure of a suppressor tRNA$^{Tyr}$ originating in *E. coli* tRNA$^{Tyr}$ (SEQ ID NO: 33) and suppressor tRNA$^{Tyr}$ originating in *Bacillus stearothermophilus* tRNA$^{TYr}$ (SEQ ID NO: 34).

As shown in FIG. 2, although *E. coli* suppressor tRNA$^{Tyr}$ has a box B consensus sequence in its sequence, it does not contain a box A consensus sequence. Accordingly, in order to express this *E. coli* suppressor tRNA$^{Tyr}$ in eukaryotic cells, U9 and C10 were substituted with A and G, respectively, to create a consensus sequence of box A (FIG. 2), and the resulting mismatch base pairs, G10 and G25, were corrected by G25C substitution. Whereupon, as shown in the comparative examples to be described later, suppressor activity failed to be detected even when combined with the aforementioned mutant *E. coli* TyrRS.

On the other hand, since the suppressor tRNA$^{Tyr}$ from *Bacillus stearothermophilus*, another prokaryote, originally has box B and box A within its sequence (M. Sprinzl, et al., Nucleic Acids Research, 17, 1-172 (1989)) (see FIG. 2), it was thought that it could be expressed in eukaryotes without any alterations.

Then, *B. stearothermophilus* suppressor tRNA$^{Tyr}$ was cloned to a vector for its introduction into animal cells without any alterations. It was, in fact, expressed in animal cells (refer to the examples described later), and exhibited suppression activity when combined with the aforementioned *E. coli* TyrRS (refer to the examples to be described later).

Namely, prokaryotic suppressor tRNA, which is able to retain suppressor activity in its form that has a box A sequence and box B sequence, can exhibit suppressor activity in eukaryotes when combined with the aforementioned *E. coli* mutant TyrRS.

Thus, the suppressor tRNA used in the expression method of the present invention is suppressor tRNA originating in *Bacillus* species, *Mycoplasma* species or *Staphylococcus* species of eubacteria and capable of binding with tyrosine derivatives in the presence of the aforementioned mutant TyrRS.

These tRNAs have a suppressor tRNA sequence that functions in prokaryotes as well as two internal promoter consensus sequences that are recognized in eukaryotes, and are capable of binding with tyrosine derivatives in the presence of the aforementioned mutant TyrRS. Here, "having a suppressor tRNA sequence that functions in prokaryotes" means that they are suppressor tRNA originating in a prokaryote and retain an anticodon complementary to a nonsense codon (usually an amber code (UAG)) and three-dimensional structure (L-shaped structure) for functioning as suppressor tRNA. "Having two internal promoter sequences that are recognized in eukaryotes" means that these genes contain the aforementioned box A consensus sequence (SEQ. ID NO. 13) and box B consensus sequence (SEQ. ID NO. 14 or SEQ. ID NO. 20). "Being capable of binding with tyrosine derivatives in the presence of the aforementioned mutant TyrRS" means that they are suppressor tRNA capable of being recognized by mutant TyrRS and of binding with tyrosine derivatives. They are suppressor mutants derived from tRNA$^{Tyr}$ that binds with tyrosine, and capable of binding with tyrosine derivatives, and preferably position 3-substituted tyrosine in the presence of mutant TyrRS.

Examples of suppressor tRNA originating in *Bacillus* species, *Mycoplasma* species or *Staphylococcus* species of eubacterial tRNA$^{Tyr}$ include suppressor tRNA originating in tRNA$^{Tyr}$ of *Bacillus stearothermophilus*, suppressor tRNA originating in tRNA$^{Tyr}$ of *Bacillus subtilis* (see registration no. DY1540; E. F. Wawrousek, et al., (1984) J. Biol. Chem. 259, 3694-3702), suppressor tRNA originating in tRNA$^{Tyr}$ of *Mycoplasma caprocolum* (see registration no. 1140; Y. Andachi, et al., (1987) Proc. Natl. Acad. Sci. USA 84, 7398-7402), and suppressor tRNA originating in tRNA$^{Tyr}$ of *Staphylococcus aureus* (see registration no. DY1480; C. Green (1993) J. Bacteriol. 175, 5091-5096), Suppressor tRNA originating in tRNA$^{Tyr}$ of *Bacillus stearothermophilus* is used preferably.

(3) Expression of Mutant TyrRS and Suppressor tRNA in Animal Cells

Any known expression system can be used to express mutant TyrRS in animal cells, examples of which include commercially available pcDNA3.1 (Invitrogen), pAGE107 (Cytotechnology, 33 (1990)), and pAGE103 (J. Biochem. 101, 1307 (1987)). Suppressor tRNA can be expressed in animal cells using any known vector for cloning in *E. coli*, an example of which is pBR322 (Sutcliffe, J. G., Proc. Natl. Acad. Sci. USA 75, 3737-3741 (1978)).

A vector for inducible expression can be used, if necessary, for the mutant TyrRS, an example of which is the vector carrying a tetracycline-responsible promoter commercially available from Clontech or Invitrogen.

Examples of methods for introducing the vector into the cells include electroporation (Chu, Nucl. Acids Res. 15, 1311-1326 (1987)), calcium phosphate method (Chen, Mol. Cell. Biol. 7, 2745-2752 (1987)), and lipofection (Derijard, Cell 7, 1025-1037 (1994); Lamb, Nature Genetics 5, 22-30 (1993)).

(4) Proteins into which Non-Naturally-Occurring Amino Acids are Incorporated

There are no limitations on the type of protein into which a non-naturally-occurring amino acid is incorporated in the present invention. This protein may be any protein able to be expressed, and may also be a recombinant protein.

In the present invention, it is necessary to insert a nonsense codon at the location where the non-naturally-occurring amino acid is incorporated (this nonsense codon is amber codon when the suppressor tRNA is an amber suppressor). A non-naturally-occurring amino acid is then specifically incorporated at this nonsense codon (amber codon) site.

Although there are no particular limitations on the method for site-specifically inserting a mutation into a protein, and known methods can be used, it can be carried out appropriately in compliance with, for example, the methods described in Hashiomoto-Gotoh, Gene 152, 271-275 (1995), Zoller, Methods Enzymol. 100, 468-500 (1983), Kramer, Nucleic Acids Res. 12, 9441-9465 (1984), Kunkel, Proc. Natl. Acad. Sci. USA 82, 488-492 (1985) or Cellular Engineering Supplement, "New Cellular Engineering Experimental Protocols", Shujunsha, 241-248 (1993), or methods that use the "QuickChange Site-Directed Mutagenesis Kit" (Stratagene).

Since the present invention enables expression in animal cells, it enables non-naturally-occurring amino acids to be incorporated in proteins that were not expressed, only expressed in small amounts, or were unable to be subjected to modification following translation as a result of becoming an active form in *E. coli* or cell-free protein systems. A variety of such proteins are known among persons with ordinary skill in the art; examples of proteins into which non-naturally-occurring amino acids are incorporated include, but are not limited to, human epithelial growth factor receptor extracellular domain (H. Ogiso, et al., Cell 110, 775-787 (2002)), human Groucho/TLEI protein (L. Pickeles, et al., Structure 10, 751-761 (2002)) and rat muscle-specific kinase (J. Till, et al., Structure 10, 1187-1196 (2002)).

In addition, in the method of the present invention, since alloproteins are expressed in animal cells, non-naturally-occurring amino acids can also be incorporated into glycoproteins bound to sugar chains. The expression systems with animal cells, included in this invention, are particularly useful for preparing the alloproteins with sugar chains added in a native and desired pattern, in the case that these proteins have an unnatural pattern for sugar chain addition when prepared by cell-free translation systems.

(5) Host

Another aspect of the present invention is the animal cells that can be employed in the expression method included in the present invention and into that the aforementioned aaRS and suppressor tRNA, and a protein gene with a nonsense codon at the site for a non-naturally-occurring amino acid.

Mammalian cell lines for that the method to express recombinant genes have been established are preferable for the host animal cells used in the present invention. Examples of useful mammalian host cell lines include Chinese hamster ovary (CHO) and COS cells. Particular examples include simian kidney CV1 line transformed by SV40 (COS-7, ATCC CRL 1651), human embryonic kidney line (293 or subcloned 293 cells for growth in suspended media, Graham, et al., J. Gen. Virol., 36: 59 (1977)), Chinese hamster ovary cells/–DHFR (CHO, Urlaub and Chasin, Proc. Natl. Acad. Sci. USA, 77: 4216 (1980)), mouse Sertoli cells (TM4, Mather, Biol. Reprod., 23: 243-251 (1980)), human lung cells (W138, ATCC CCL 75), human liver cells (Hep G2 HB 8065), and mouse breast cancer (MMT 060562, ATCC CCL 51). Since the expression systems for extragenic genes have been established for these hosts, the selection of appropriate host cells is within the technical scope of a person with ordinary skill in the art.

The expression of extragenic genes in these host cells can be carried out according to the methods described in, for example, Molecular Cloning, 2nd edition, Cold Spring Harbor Laboratory Press (1999).

An explanation is provided with reference to FIG. 1 of how a non-naturally occurring amino acid can be incorporated into proteins according to the aforementioned expression method of the present invention. The enclosure shown in FIG. 1 represents the cell membrane of a mammalian cell (e.g., Chinese hamster ovary cells (CHO cells)). Inside the cell (inside the enclosure), suppressor tRNA$^{Tyr}$ (indicated as "B.s. tRNA$^{Tyr}$") and aaRS (indicated as "*E. coli* mutant TyrRS") are expressed from their respective expression systems. The non-naturally-occurring amino acid. 3-iodo-L-tyrosine, here, is added to the medium (outside the enclosure).

The 3-iodo-L-tyrosine in the medium is taken up by the cell due to the activity of the cell itself, and binds to B.s. tRNA$^{Tyr}$ due to the function of *E. coli* mutant TyrRS. Subsequently, the 3-iodo-L-tyrosine is transported to ribosomes by B.s. tRNA$^{Tyr}$ where this amino acid is used to translate a nonsense codon (here, a UAG codon). In order to produce a protein that contains 3-iodo-L-tyrosine at a desired position, the codon at this position of the protein gene is replaced by UAG. This gene is then expressed in the cell.

In this manner, the expression method of the present invention makes it possible to express in a animal cells a desired protein in that a tyrosine derivative has been incorporated at a desired position.

Namely, animal cells having:

(A) an expression vector that expresses in animal cells mutant TyrRS that is a derivative of TyrRS originating in *E. coli* with an enhanced specificity for a non-naturally-occurring tyrosine derivative as compared with specificity for tyrosine (B) an expression vector that expresses in the aforementioned animal cells suppressor tRNA originating in *Bacillus* species, *Mycoplasma* species or *Staphylococcus* species of eubacteria and capable of binding with the aforementioned tyrosine derivative in the presence of the mutant TyrRS; and, (C) a desired protein gene that has undergone a nonsense mutation at a desired site; are incubated under suitable conditions in a medium suitable for the growth of animal cells (e.g., Opti-MEM I (Gibco BRL) in the case of CHO cells) to which a desired tyrosine derivative has been added. For example, in the case of CHO cells, the aforementioned cells are incubated for about 24 hours at a temperature of about 37°

C. The concentration of a tyrosine derivative added to the medium is about 0.1 to 3 mM and preferably about 0.3 mM.

A different aspect of the present invention is a production method for a non-naturally-occurring amino acid-containing protein, by which alloprotein is expressed according to the aforementioned expression method to be recovered and purified.

The expressed protein can be recovered from medium or a host cell lysate. If it is bound to a membrane, then it can be separated from the membrane by using a suitable washing solution (e.g., Triton-X 100) or by enzymatic severing. The cells can be lysed by various physicochemical means such as freeze-thaw cycling, ultrasonic treatment, mechanical crushing or using a cytolytic agent.

In the case that the expressed protein forms an insoluble aggregation, this aggregate can be solved with a denaturant for protein and then subjected to the process of refolding of denaturing protein, for example, in a solution without denaturant or containing the denaturant in too low a concentration to denature the protein, or by dialysis.

Isolation and purification of the protein can be carried out, considering the characteristic properties of the protein produced, by using any or some, in combination, of solvent extraction, fractional precipitation using organic solvent, salting out, dialysis, centrifugal separation, ultrafiltration, ion exchange chromatography, gel filtration chromatography, hydrophobic chromatography, affinity chromatography, reverse phase chromatography, crystallization, electrophoresis and other separation procedures.

Another aspect of the present invention is DNA having the following sequence of SEQ. ID NO. 1.

```
                                              (SEQ. ID NO. 1)
AGCGTCCGGTTTTTCTGTGCTGAACCTCAGGGGACGCCGACACACGTACA

CGTCGGAGGGGTAGCGAAGTGGCTAAACGCGGCGGACTCTAAATCCGCTC

CCTTTGGGTTCGGCGGTTCGAATCCGTCCCCCTCCAGACAAGTGCGGTTT

TTTTCTCCAGCTCCCG
```

This sequence of SEQ. ID NO. 1 is an artificial base sequence consisting of a leader sequence of human tRNA gene (bases 1 to 55 of SEQ. ID NO. 1), the tRNA$^{Tyr}$ gene of *B. stearothermophilus* with a CUA anticodon (underlined portion; bases 56 to 137 of SEQ. ID NO. 1) but without the terminal CCA sequence and a transcription terminator (bases 138 to 167 of SEQ. ID NO. 1) in this codon.

DNA having the sequence of SEQ. ID NO. 1 can be inserted into a replicating vector for cloning (amplification of that DNA) or expression. Various types of vectors can be used. Said vector can be in the form of a plasmid, cosmid, virus particle or phage. Desired nucleic acid sequences can be inserted into said vector by various techniques. In general, DNA is inserted at a suitable restriction site using technology known in the art. There are no limitations on the use of vector elements; the vector typically includes one or more signal sequences, replication origins, marker genes and so forth. The construction of a suitable vector containing one or more of these elements is a known technology among persons with ordinary skill in the art.

Suppressor tRNA can be expressed in animal cells by introducing this expression vector into animal cells. Since a vector containing the sequence of SEQ. ID NO. 1 has a box A, box B and 5'-leader sequence as the regulatory sequences recognized in animal cells, when the vector was inserted into animal cells, the suppressor tRNA will be expressed in the animal cells by using these regulatory sequences when the vector was inserted into animal cells.

Thus, not only can this expression vector be used in the aforementioned expression method of a non-naturally-occurring amino acid-containing protein, but it can also be used for gene therapy for diseases related to nonsense mutations.

A cloning vector contains a nucleic acid sequence that allows replication of that vector in one or more host cells. In addition, an expression vector may contain such a sequence for replication. Such sequences are well known for various types of bacteria, yeasts and viruses. Various types of virus origins (SV40, polyoma, adenovirus, VSV or PBV) are useful for cloning vectors in mammalian cells.

Expression and cloning vectors typically contain selectable markers. Typical selection markers include ampicillin resistance gene, neomycin resistance gene, zeocin resistance gene, DHFR gene and thymidine kinase gene. Suitable host cells in the case of using wild-type DHFR are CHO cell lines lacking in DHFR activity; this cell line has been produced and grown as described in Urlaub, et al., Proc. Natl. Acad. Sci. USA, 77: 4216 (1980).

Other methods, vectors and host cells suitable for protein synthesis in cultured recombinant vertebrate cells are described in Gething, et al., Nature, 293: 620-625 (1981) and Mantei, et al., Nature, 281: 40-46 (1979).

Gene amplification and expression can be analyzed for a given sample, for example, by ordinary southern blotting, northern blotting for quantifying transcription of mRNA (Thomas, Proc. Natl. Acad. Sci. USA, 77: 5201-5205 (1980)), dot blotting (DNA analysis) or in situ hybridization using a labeled probe with the sequences provided here. Antibody can also be used capable of specifically recognizing double strands including DNA double strands, RNA double strands and DNA-RNA hybrid double strands or DNA-protein double strands. With these antibodies, which may be labeled, said assay can be carried out in the case the double strand is bound to a surface so that the presence of antibody bound to this double strand can be detected on this surface.

Gene expression can also be measured by such an immunological method as cell immunohistological staining or these applicable to tissue sections, as well as by cell culture or liquid assay in order to quantify the expression of a gene product directly. Useful antibodies for immunohistological staining of liquid samples may be either monoclonal or polyclonal antibodies, and they can be produced in any mammal.

The following provides a more detailed explanation of the present invention based on its examples; although the present invention is not limited to these examples. In the present description, the entirety of the cited documents are incorporated for reference purposes.

Example 1

Expression of Protein Containing 3-iodotyrosine

In the present example, an Ras protein in which the 32nd codon was substituted to UAG is expressed in CHO cells to produce an Ras protein containing 3-iodotyrosine at said site.

In the present example, although suppressor tRNA is expressed constitutively, expression of mutant TyrRS that binds non-naturally-occurring amino acid thereto was induced by adding tetracycline to the culture medium.

(1) Suppressor tRNA

The base sequence of the B.s. tRNA$^{Tyr}$ (167 bases) used as suppressor tRNA is as shown below.

```
                                              (SEQ. ID NO. 1)
AGCGTCCGGTTTTTCTGTGCTGAACCTCAGGGGACGCCGACACACGTACA

CGTCGGAGGGGTAGCGAAGTGGCTAAACGCGGCGGACTCTAAATCCGCTC

CCTTTGGGTTCGGCGGTTCGAATCCGTCCCCCTCCAGACAAGTGCGGTTT

TTTTCTCCAGCTCCCG
```

This sequence is an artificial base sequence consisting of a leader sequence of human tRNA gene (H. van Tol, et al., EMBO J. 6, 35-31 (1987)), the tRNA$^{Tyr}$ gene of B. stearothermophilus with a CUA anticodon (underlined portion) but without the terminal CCA sequence, and a transcription terminator (H. van Tol, et al., EMBO J. 6, 35-31 (1987)) in this order.

The single-strand DNA that possesses this SEQ. ID NO. 1 was obtained in the form of a chemically synthesized product by a widely used commercial service (Sigma Genosys Japan) that synthesizes PCR primers and other single-strand DNA. A DNA fragment amplified by PCR using this DNA as a template and the following primers (1) and (2) was cloned by severing with EcoRI and HindIII followed by incorporating at the EcoRI-HindIII site of pBR322.

```
Primer (1):
CACAGAATTCTCGGGAGCTCGAGAAAAAAAC    (SEQ. ID NO. 21)

Primer (2):
CACAAAGCTTAGCGCTCCGGTTTTTCTGTG     (SEQ. ID NO. 22)
```

Figure 3:
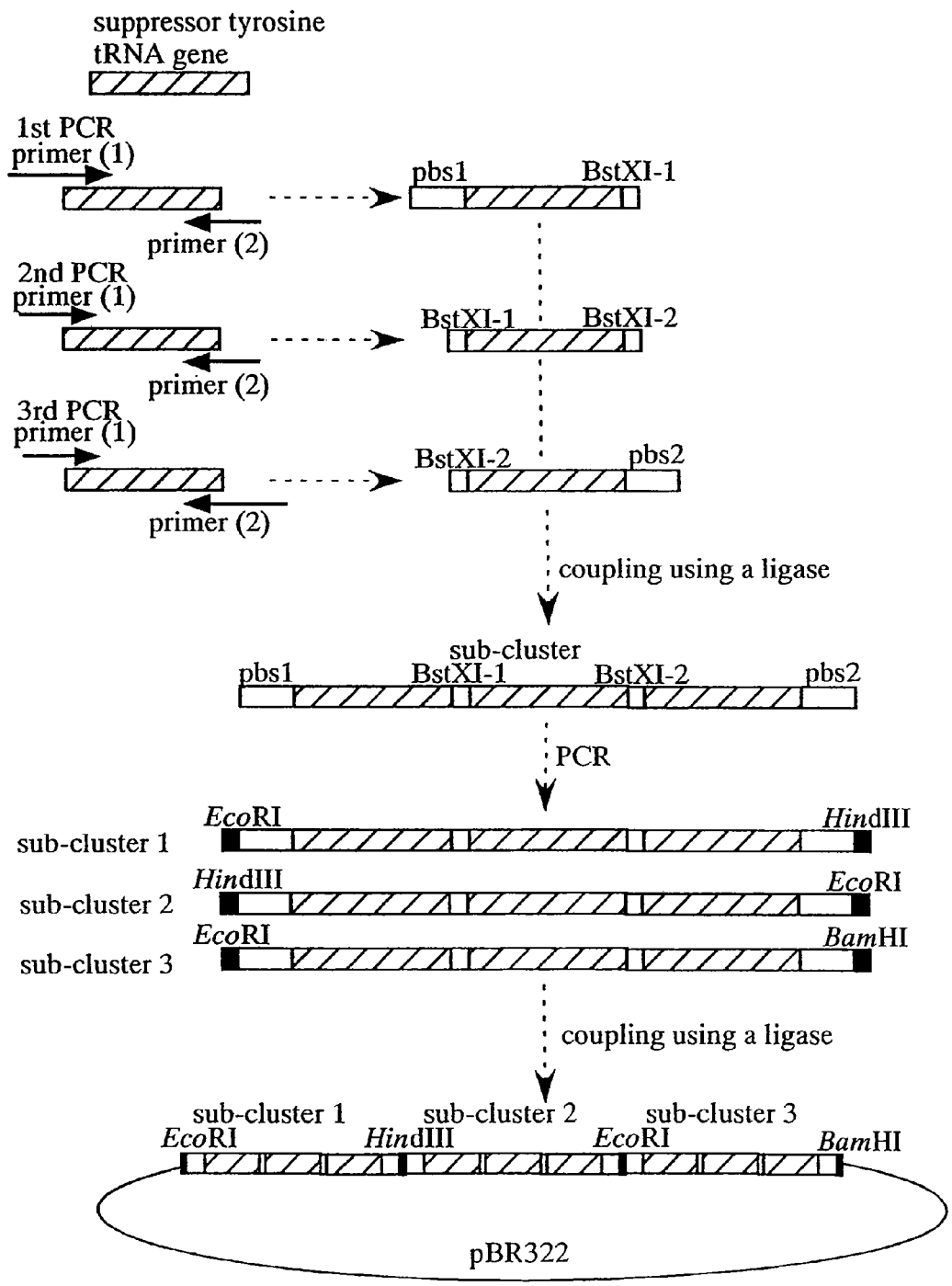
FIG. 3 is a drawing showing the structure of a plasmid having nine copies of *Bacillus stearothermophilus* suppressor tRNA$^{Tyr}$ in series.

Nine gene clusters for which the suppressor tRNA$^{Tyr}$ gene of B. stearothermophilus was copied in the same direction were constructed using the following two steps (FIG. 3).

First, PCR as described below was carried out with the GeneAmp PCR System 9700 (Applied Biosystems) using three different primer sets 1 to 3 each including primers (1) and (2)

In the first reaction, a fragment was produced having a primer binding site pbs1 (SEQ. ID NO. 15) upstream of the sequence of SEQ. ID NO. 1 and a BstXI-1 site (CCAGCAGACTGG: SEQ. ID NO. 17) downstream of this DNA, by carrying out PCR under normal reaction conditions using primer (1) of the first set:

```
                                              (SEQ. ID NO. 23)
AGCGAGTGTTAACCCTGCCTAGCGCTCCGGTTTTTCTGTG
``` and primer (2) of the first set:

```
                                              (SEQ ID NO. 24)
ACACACCCAGCAGACTGGCGGGAGCTGGAGAAAAAAAC.
```

In the second reaction, a fragment was produced having a BstXI-1 site (SEQ. ID NO. 17) upstream of the sequence of SEQ. ID NO. 1 and another BstXI site, CCAGCTTCCTGG (BstXI-2; SEQ. ID NO. 18) downstream from this sequence, by carrying out PCR under normal reaction conditions using primer (1) of the second set:

```
                                                (SEQ ID NO. 25)
    ACACACCCAGCAGACTGGAGCGCTCCGGTTTTCTGTG
``` and primer (2) of the second set:

```
                                                (SEQ. ID NO. 26)
    ACACACCCAGCTTCCTGGCGGGAGCTGGAGAAAAAAAC.
```

In the third reaction, a fragment was produced having a BstXI-2 site (SEQ. ID NO. 18) upstream of the sequence of SEQ. ID NO. 1 and the primer binding site pbs2 (SEQ. ID NO. 16 downstream of SEQ No. 1, by carrying out PCR under normal reaction conditions using primer (1) of the third set:

```
                                                (SEQ ID NO. 27)
    ACACACCCAGCTTCCTGGAGCGCTCCGGTTTTCTGTG
``` and primer (2) of the third set:

```
                                                (SEQ. ID NO. 28)
    CTGCGCGAATATCGTAGTCGCGGGAGCTGGAGAAAAAAAC.
```

These three PCR products were coupled together using a ligase according to known technology to produce a sub-cluster comprised of three copies of tRNA gene.

This sub-cluster was amplified in the form of a sub-cluster fragment to which EcoRI site was added to one end and HindIII site was added to the other end using a primer with an EcoRI restriction site added to the sequence of pbs1 (SEQ. ID NO. 15) and a primer with a HindIII restriction site was added to the sequence of pbs2 (SEQ. ID NO. 16).

Moreover, a fragment to which HindIII and EcoRI sites were added at the ends, and a sub-cluster fragment to which EcoRI and BamHI sites were added to the ends, were similarly produced. Finally, three types of sub-clusters were produced having different combinations of restriction sites. These sub-clusters 1 to 3 were coupled together with ligase, and then cloned within EcoRI and BamHI sties of pBR322 (Takara Shuzo) to produce plasmid pBstRNA having nine copies of *B. stearothermophilus* suppressor tRNA$^{Tyr}$ gene.

The structure of the resulting cloned fragment is shown in FIG. 3.

In FIG. 3, the base sequences of pbs1, pbs2, BstX-1 and BstX-2 are as shown below.

```
    pbs1:
    AGCGAGTGTTAACCCTGCCT          (SEQ. ID NO. 15)

pbs2:
    CGACTACGATATTCGCGCAG          (SEQ. ID NO. 16)

BstX-1:
    CCAGCAGACTGG                  (SEQ. ID NO. 17)

BstX-2:
    CCAGCTTCCTGG                  (SEQ. ID NO. 18)
```

Since plasmid pBstRNA has nine copies of *B. stearothermophilus* suppressor tRNA$^{Tyr}$ gene, the amount of *B. stearothermophilus* suppressor tRNA$^{Tyr}$ gene expressed in animal cells can be increased, and is useful for expressing alloproteins in animal cells.

(2) Mutant TyrRS

The base sequence of *E. coli* mutant TyrRS (to be referred to as TyrRS(V37C195) gene is described in Document 5.

In the aforementioned method, a DNA sequence that encodes a single amino acid-substituted form in which a single amino acid at position 37 or 195 is substituted was produced using the aforementioned primers (3) to (8). Primers (3) and (4) are for altering position 37. In addition, primers (5) to (8) are for altering position 195.

Next, two fragments were amplified with primer pair (1) and (10) and primer pair (9) and (11), using the plasmid that encodes a single amino acid-substituted TyrRS at positions 37 and 195, respectively. The two fragments were purified and then coupled by PCR using primers (1) and (9).

The PCR amplification product was inserted into the multiple cloning site of vector pcDNA4/TO (Invitrogen) to create plasmid pEYSM1.

(3) Amber Suppression in Mammalian Cells

Transfection was carried out using 0.5 to 2 μg of DNA for each plasmid per 35 mm plate in accordance with the Lipofect AMINE 2000 (Gibco BRL) method. Opti-MEM 1 (Gibco BRL) was used for the medium. Cell extracts were prepared 24 hours after transfection and applied to SDS-PAGE followed by western blotting using anti-FLAG2 antibody (Sigma) and the ECL+ Immunodetection System (Amersham Pharmacia Biotech). Band intensity was measured using the LAS-1000plus image analyzer (Fuji Film). The ras(Am) products and a wild type ras product for comparison (0.5 μg each) were each purified, using anti-FLAG M2 antibody affinity gel (Sigma), from 1 to 5 culture plates (diameter: 100 mm). This was followed by liquid chromatography-electrospray mass analysis (LC-MS) and tandem mass analysis sequencing.

(4) CHO-Y Cells

In order to create CHO-Y cells that stably retain TyrRS (V37C195), T-REX-CHO cells that constitutively produce tetracycline repressor protein (Invitrogen) were transfected with plasmid pEYSM1. The transfectants were selected in medium containing 25 μg/ml of zeocin, and the expression of TyrRS (V37C195) in the selected cells in the presence of 1 μg/ml of zeocin was checked to obtain CHO-Y cells. In order to synthesize alloprotein, the CHO-Y cells were transfected with a plasmid containing ras(Am) and *B. stearothermophilus* suppressor tRNA$^{Tyr}$ gene. Tetracycline (1 μg/ml) and 3-iodo-L-tyrosine (0.3 mM) were added to the medium 24 hours after transfection and a cell extract was prepared after further 24 hours.

(5) Incorporation of 3-iodo-L-tyrosine at Amber Codon

The following two points were taken into consideration to incorporate 3-iodo-L-tyrosine in protein. Firstly, mammalian cells have a transport mechanism by which inherent amino acids and their various analogs are taken up from the environments. Secondly, wild type TyrRSs from eukaryotes and prokaryotes do not recognize 3-iodo-L-tyrosine as substrate. Therefore, cells do not suffer from the toxicity resulting from at-random 3-iodo-L-tyrosine incorporation at tyrosine positions. Mutant TyrRS that is able to recognize 3-iodo-tyrosine is required to bind this amino acid to the suppressor tRNA.

We therefore used *E. coli* TyrRS (V37C195), which has been reported to efficiently recognize 3-iodo-L-tyrosine ($K_{cat}/K_m$ value for amino acid activation=$3.3\times10^3$/M/s) and recognize tyrosine at a sufficiently low efficiency ($K_{cat}/K_m$ value=$3.2\times10^2$/M/s). Moreover, TyrRS (V37C195) activates L-tyrosine at an efficiency roughly 10,000 times lower as compared with the $K_{cat}/K_m$ value ($2.3\times10^6$/M/s) with respect to the wild type enzyme.

Figures 5A, 5B:
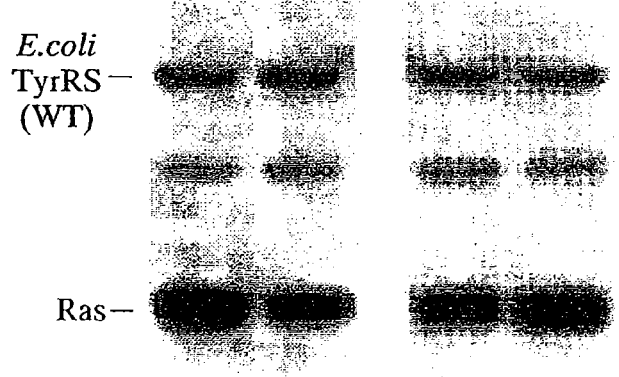
FIGS. 5A and 5B are photographs of western blots for detecting amber suppression.

FIGS. 5A and 5B are photographs of western blotting for detecting amber suppression. FIG. 5A shows western blotting in the absence of 3-iodo-L-tyrosine, while FIG. 5B shows it in the presence of 3-iodo-L-tyrosine. The ras(Am) gene was introduced at all lanes. The wild type *E. coli* TyrRS (lane 1 in A and B) or TyrRS (V137C195) (lane 2 in A and B) were expressed in CHO cells together with *B. stearothermophilus* suppressor tRNA$^{Tyr}$. The presence or absence of 3-iodo-L-tyrosine (IY) and the type of TyrRS expressed (wt for TyrRS wild type and mut for TyrRS (V37C195) are indicated.

As shown in FIGS. 5A and 5B, wild type TyrRS and TyrRS (V37C195) were each expressed in CHO cells together with *B. stearothermophilus* suppressor tRNA$^{Tyr}$ and ras(Am) gene. These enzymes were expressed at the same levels. Although amber suppression was observed for both enzymes in the absence of 3-iodo-L-tyrosine (FIG. 5A), the yield of the ras(Am) product with TyrRS (V37C195) was only 40% of the wild type enzyme. This indicates that even in the absence of competitive 3-iodo-L-tyrosine, TyrRS (V37C195) recognizes L-tyrosine and incorporates it at the amber location. Next, 3-iodo-L-tyrosine was added to the medium to a final concentration of 0.3 mM (L-tyrosine was present at twice that concentration (FIG. 5B)). This concentration of 3-iodo-L-tyrosine had hardly any effect on cell reproduction.

In the presence of 3-iodo-L-tyrosine, the suppression efficiency with TyrRS (V37C195) was improved to a level comparable to that with the wild type enzyme. Thus, 3-iodo-L-tyrosine was efficiently taken up by the cells, to be incorporated into protein depending on TyrRS (V37C195).

(6) Confirmation of Ras Products

In order to confirm the incorporation of 3-iodo-L-tyrosine at the amber location (position 32), the ras product was degraded by *Achromobacter* protease I (Lys-C). The resulting degradation product in the form of a peptide mixture was analyzed using a liquid chromatography-mass analyzer (LC-MS). Then, the amino acid incorporated at position 32 was identified on the basis of the specific average mass and the elution time in liquid chromatography. The fragment corresponding to the sequence from serine at position 17 to lysine at position 42 was called the IY and Y fragments according to the presence of iodotyrosine and tyrosine, respectively, at position 32.

Figure 6A:
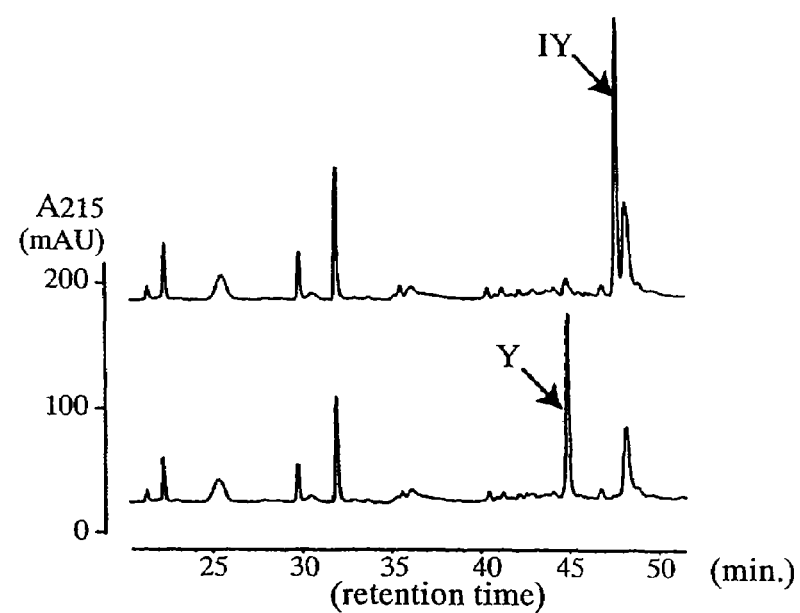
FIGS. 6A, 6B and 6C are graphs showing the results of LC-MS analysis of ras and ras(Am) products.
Figure 6B:
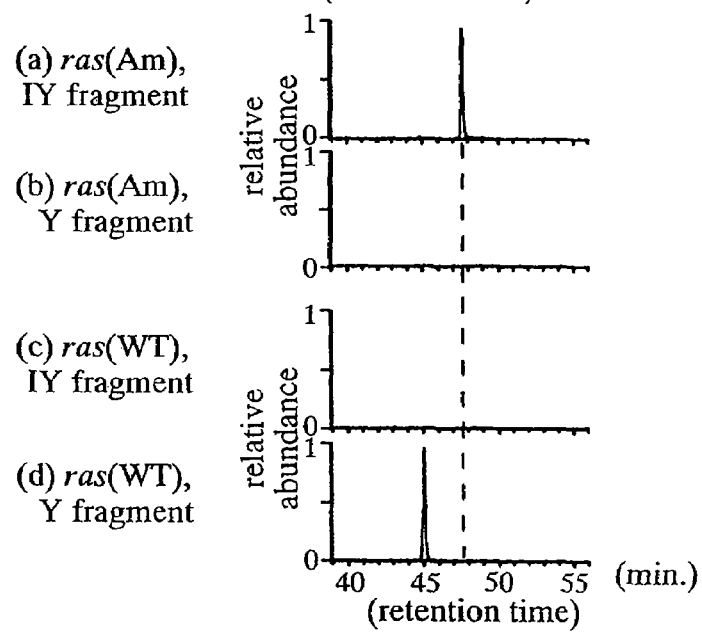
Figure 6C:
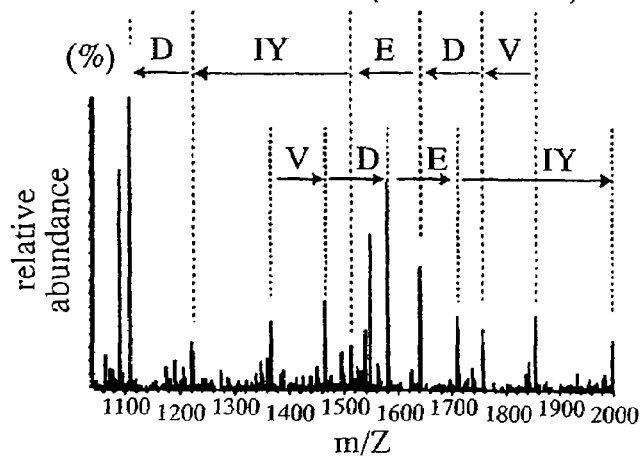

FIGS. 6A, 6B and 6C are graphs showing the results of LC-MS analysis of the ras and ras(Am) products.

FIG. 6A shows the results of liquid chromatography in which the ras(Am) fragments (Chart A) and the ras fragments (Chart B) were detected based on their UV absorbance.

FIG. 6B shows the results of the mass spectrometry for the IY fragment (Charts a and c) and Y fragment (Charts b and d) from the ras(Am) product (Charts a and b) and ras product (Charts c and d). The Y fragment is composed of residues 17 to 42 of Ras protein (SALTIQLIQNHFVDE YDPTIEDSYRK), while the IY fragment has 3-iodo-L-tyrosine substituting for the underlined Y.

FIG. 6C shows the results of tandem mass spectrometry of the IY fragment. The partial sequence in the direction of the C-terminal from the N-terminal consists of Val, Asp, Glu, iodotyrosine and Asp.

During analysis of the ras(Am) product, the IY fragment was strongly observed (FIG. 6B, Chart A), indicating efficient incorporation of 3-iodo-L-tyrosine. The partial sequence of this IY fragment as determined by tandem mass spectrometry confirmed that iodotyrosine was actually incorporated at position 32 (FIG. 6C). On the other hand, it was also shown that the Y fragment was not detected (FIG. 6B, Chart b); 3-iodo-L-tyrosine thus inhibited the incorporation of L-tyrosine at position 32. Further analysis of the LC-MS data indicated that other normal amino acids were not incorporated at this position. The incorporation of iodotyrosine at position 32 was thus confirmed by LC-MS analysis. In contrast, although the Y fragment was observed for the ras(WT) product synthesized in the presence of 3-iodo-L-tyrosine (Chart d), while the IY fragment was not observed (FIG. 6B, Chart c). Since 3-iodo-L-tyrosine would be incorporated at the location of tyrosine by any recognition error, this observation indicates that intrinsic TyrRS in CHO cells does not recognize 3-iodo-L-tyrosine, nor does TyrRS (V37C195) recognize intrinsic tRNA$^{Tyr}$.

As shown in FIG. 6B, the peak of a peptide that contains 3-iodo-L-tyrosine was detected (FIG. 6B(a)). On the other hand, if the UAG codon is assumed to be translated to an amino acid other than 3-iodo-L-tyrosine, it is most likely that it would be translated to tyrosine; in fact, a peptide that contained tyrosine was not detected (FIG. 6B(b)). In addition, peptides that could be produced if the UAG codon had been translated to another amino acid were not detected at all.

These results indicate that nearly 100% of the Ras protein produced contained 3-iodo-L-tyrosine at the location specified by the UAG codon, and that the present invention yields the expected effects.

(7) Conditioned Incorporation of 3-iodo-L-tyrosine Controlled by Inducible Expression of Mutant TyrRS It has been reported that *E. coli* GlnRS causes induced suppression by being expressed from a tetracycline control promoter in mammals. We created a CHO cell line (referred to as CHO-YS cells) that stably retain the TyrRS (V37C195) gene expressed from another type of tetracycline-controlled promoter. The ras(Am) gene and *B. stearothermophilus* suppressor tRNA$^{Tyr}$ gene were then transiently introduced into the CHO-YS cells.

FIG. 7 is a photograph of a western blot of inducible amber suppression for the incorporation of 3-iodo-L-tyrosine by Ras protein. The ras(Am) gene was introduced into CHO-Y cells. The ras(Am) gene was introduced into CHO-Y cells together with *B. stearothermophilus* suppressor tRNA$^{Tyr}$ (lanes 1-3). Lane 1 indicates the addition of tetracycline and 3-iodo-L-tyrosine, lane 2 the addition of tetracycline without the addition of 3-iodo-L-tyrosine, and lane 3 the absence of the addition of tetracycline or 3-iodo-L-tyrosine.

As shown in FIG. 7, TyrRS (V37C195) was expressed when tetracycline was present in the medium (FIG. 7, lanes 1 and 2), but was not expressed in the absence of an inducer (lane 3). The level of expression was twice the level of TyrRS (V37C195) expressed from a plasmid transiently introduced into the cells. The ras(Am) product was detected at a suppression efficiency of 30% in the presence of both 3-iodo-L-tyrosine and tetracycline (lane 1). The quality of the ras(Am) product was indicated as being identical to the quality of ras(WT) similarly produced in CHO-Y cells, and the quality in the presence of TyrRS (V37C195) from plasmid as analyzed by LC-MS. More than 95% of the ras(Am) product % contained 3-iodo-L-tyrosine at the amber position, while 3-iodo-L-tyrosine was not detected in the ras(WT) product.

On the other hand, the ras(Am) product was hardly detected in the absence of 3-iodo-L-tyrosine (lane 2), and was not detected in the absence of inducer (lane 3). These observations indicated that the incorporation of 3-iodo-L-tyrosine into the ras(Am) product is effectively conditioned by means of the induction of the expression of TyrRS (V37C195) by tetracycline. A comparison of FIG. 7 and FIG. 5A indicates that the incorporation of L-tyrosine in the absence of 3-iodo-L-tyrosine is remarkably lower than in the case of having expressed TyrRS (V37C195) from a plasmid. This unexpected result was observed in three or more independent observations. The mechanism on which this phenomenon is based is a subject for further research.

Example 2

(1) Suppressor tRNA Inducible Expression System

The eukaryotic transcription of tRNA involves the formation of a transcription complex upon the transcription promoter sequences (boxes A and B) within the tRNA gene. If a protein factor binds to the sequence immediately before the tRNA gene, this factor would inhibit the expression of tRNA by obstructing the formation of the transcription complex. Previously, expression of tRNA has been successfully inhibited in yeast and Myxomycetes by incorporating $tetO_1$, which is one of the binding sequences for the tetracycline-binding repressor, immediately before the tRNA gene (T. Dingerman, et al., EMBO Journal 11, 1487-1492 (1992); T. Dingerman, et al., Mol. Cell. Biol. 12, 4038-4045 (1992)). The concentration of the tetracycline added to the culture liquid at that time was 15-30 μg/mL.

In this example, an attempt was made to induce expression at a lower concentration of tetracycline with the intention of reducing cytotoxicity. Consequently, three types of induced expression systems were prepared by incorporating a $tetO_2$ sequence, which binds repressor more strongly, instead of $tetO_1$, immediately before, or 10 or 20 bases upstream from, the suppressor tRNA gene (TetBst0 (Sequence 1; SEQ. ID NO. 30), TetBst1 (Sequence 2; SEQ. ID NO. 31), TetBst2 (Sequence 3; SEQ. ID NO. 32)).

```
TetBst0
                         (Sequence 1; SEQ. ID NO. 30)
TCTCCCTATCAGTGATAGAGATCGGAGGGGTAGCGAAGTGGCTAAA

CGCGGCGGACTCTAAATCCGCTCCCTTTGGGTTCGGCGGTTCGAA

TCCGTCCCCCTCCAGACAAGTGCGGTTTTTTTCTCCAGCTCCCG
```

The first underlined portion indicates the $tetO_2$ sequence, while the next underlined portion indicates the suppressor tRNA gene.

```
TetBst1
                         (Sequence 2; SEQ. ID NO. 31)
TCTCCCTATCAGTGATAGAGATCCGTACACGTCGGAGGGGTAGCGAA

GTGGCTAAACGCGGCGGACTCTAAATCCGCTCCCTTTGGGTTCGGCGGTT

CGAATCCGTCCCCCTCCAGACAAGTGCGGTTTTTTTCTCCAGCTCCCG
```

The first underlined portion indicates the $tetO_2$ sequence, while the next underlined portion indicates the suppressor tRNA gene.

```
TetBst2
                         (Sequence 3; SEQ. ID NO. 32)
TCTCCCTATCAGTGATAGAGATCCGCCGACACACGTACACGTCGGAGGGG

TAGCGAAGTGGCTAAACGCGGCGGACTCTAAATCCGCTCCCTTTGGGTTC

GGCGGTTCGAATCCGTCCCCCTCCAGACAAGTGCGGTTTTTTTCTCCAGC

TCCCG
```

The first underlined portion indicates the $tetO_2$ sequence, while the next underlined portion indicates the suppressor tRNA gene.

The suppression efficiencies were compared among these sequences together with the sequences consisting of three copies of TetBst0 and TetBst1.

Figure 9:
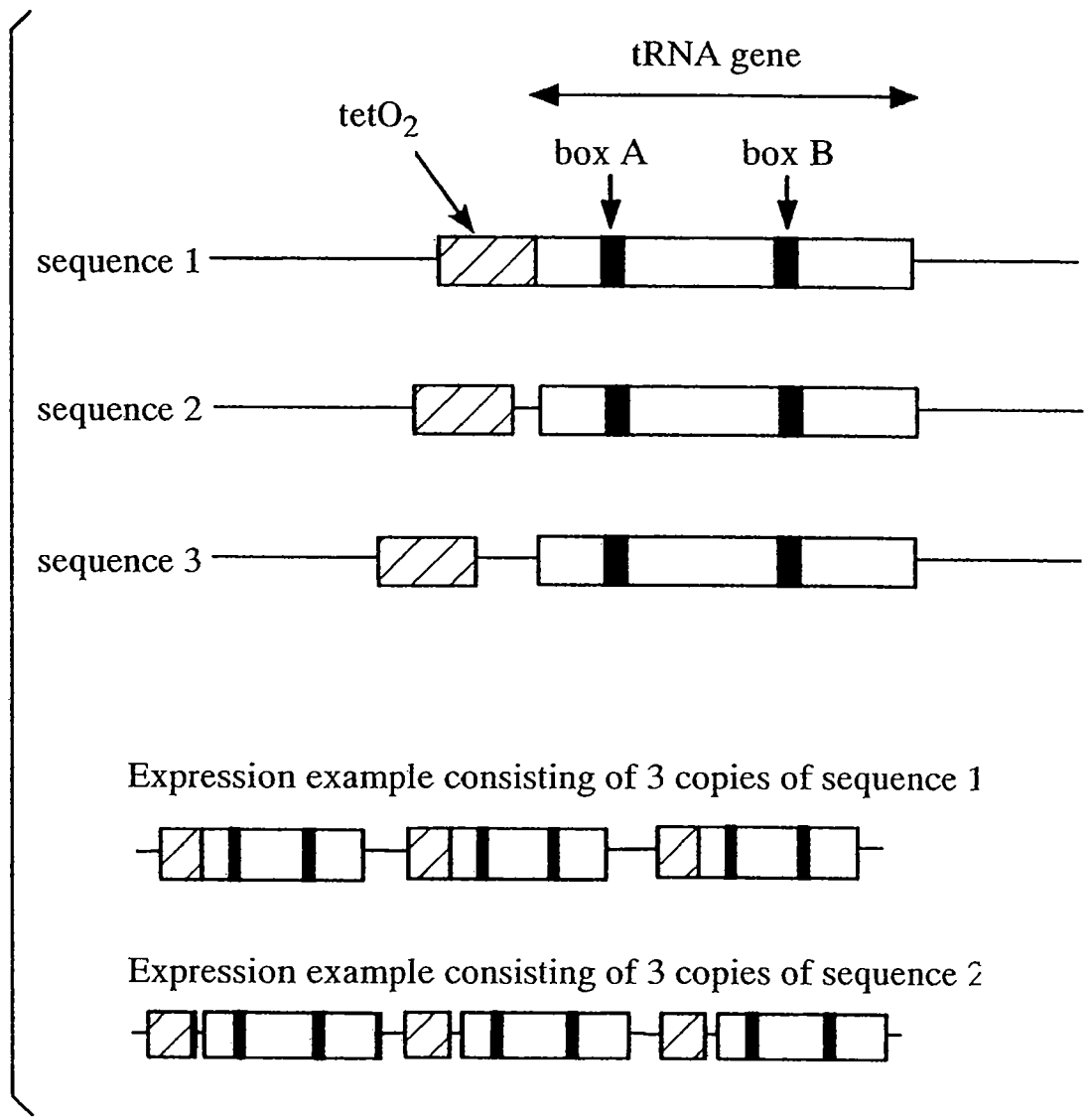
FIG. 9 is a schematic drawing of TetBst0, TetBst1 and TetBst2.

The aforementioned TetBst0, TetBst1 and TetBst2 were respectively cloned to the EcoRI-HindIII site of plasmid pBR322. The sequences consisting of three copies of sequences 1 (TetBst0) and 2 (TetBst1) were also similarly cloned (FIG. 9). The introduction of plasmids into the cultured cells and detection of the suppression products were carried out in similar manners as Example 1(5).

The expression of suppressor tRNA was induced by the addition of tetracycline at 1 μg/mL, thereby demonstrating that the concentration of tetracycline can be decreased. This is useful for reducing cytotoxicity.

Since the suppression efficiency of TetBst2 was lower than that of TetBst1 (data not shown), suppression efficiency was analyzed for TetBst0 and TstBst1 in detail, and for the sequences comprising the three copies of sequences 1 and 2 (3×TetBst0 and 3×TetBst1). At the same time, a comparison was also made with the gene comprising nine copies of amber suppressor tRNA gene (BYR(CUA)) prepared in Example 1. Those results are shown in FIGS. 10A and 10B.

Figure 10A:
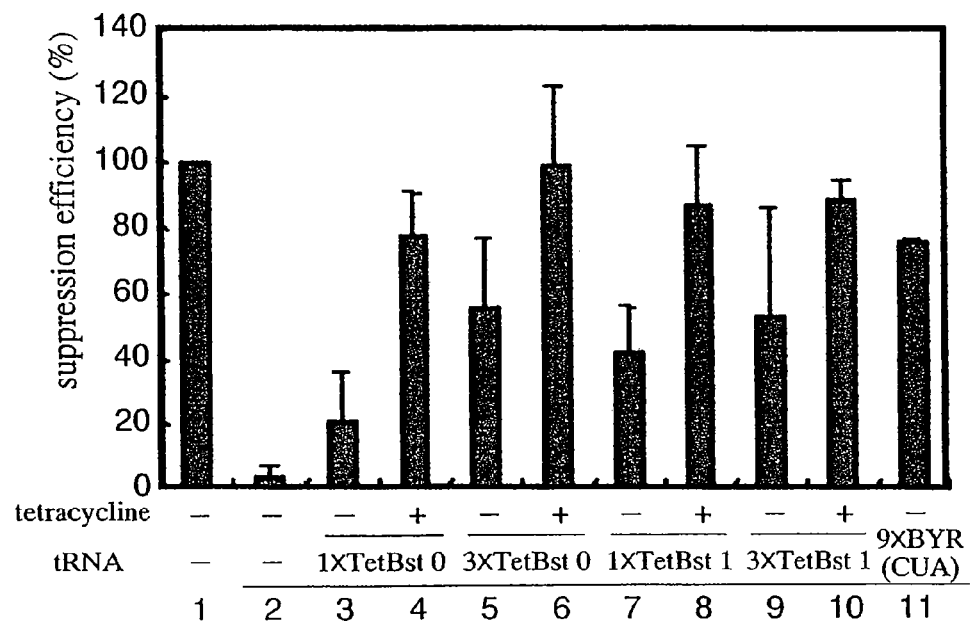
FIGS. 10A and 10B show the results of comparing suppression efficiency in examples of the present invention.
Figure 10B:
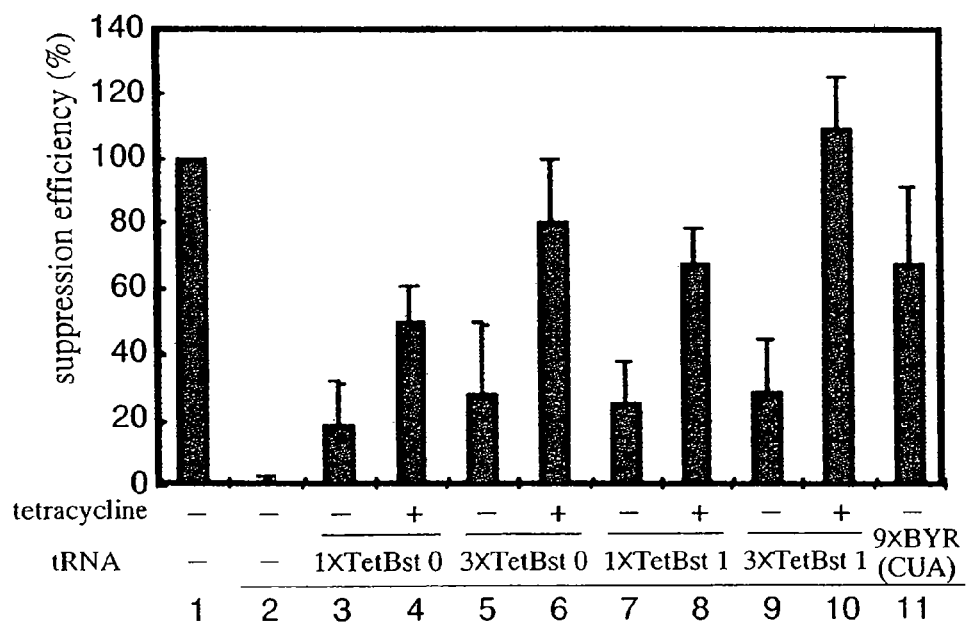

The respective amounts of Ras protein produced by the amber mutant are shown in FIG. 10A, while the amounts of EGF receptor (EGFR) produced by the amber mutant are shown in FIG. 10B. The amounts produced were measured based on the band intensities of western blots and were then graphed in the form of their suppression efficiencies. The graphs were produced based on three sets of experimental data each. Lane 1 shows the amounts of wild type Ras protein and wild type EGFR produced that do not have an amber codon, and the other suppression efficiencies were quantified by assigning a value of 100 to this value. However, since the band intensity of the wild type protein exceeded the measurement limit and is presumed to actually exceed 100, only the suppression efficiency of 9×BYR(CUA) and a comparison of the efficiencies of TetBst are discussed here. On the basis of other experiments, the suppression efficiencies of Ras mutant and EGFR mutant by 9×BYR(CUA) were found to be 24% and 20%, respectively (Sakamoto, et al., Nucleic Acids Research 30, 4692-4699 (2002)).

Suppression can be seen to be induced with the addition of tetracycline at 1 μg/mL. On the other hand, suppression is also observed to a certain degree even in the absence of tetracycline addition. TetBst1 tended to show a higher suppression efficiency than TetBst0, three gene copies tended to show a higher suppression efficiency than a single gene copy, and the same trends were observed in the absence of tetracycline as well. The efficiency for 3×TetBst1 was significantly higher than that for 9×BYR(CUA), and is advantageous for the production of non-naturally-occurring amino acid-containing protein. The nearly complete absence of suppression was observed, when tetracycline is not added in the case of using TetBst0×1. Therefore, the use of TetBst0×1 is believed to be the most advantageous for avoiding cytotoxicity.

In general, amber suppression could cause cytotoxicity in animal cells. Consequently, suppression using suppressor tRNA that is constitutively expressed has the possibility of increasing the number of dead cells.

In Example 1, although suppressor tRNA is expressed continuously, expression of TyrRS that binds non-naturally-occurring amino acids thereto was induced by adding tetracycline to the culture liquid. Namely, since tRNA does not cause suppression unless it binds amino acid, cytotoxicity was intentionally reduced by expressing TyrRS only when this enzyme is required to produce protein containing non-naturally-occurring amino acid. However, since there is no guarantee that B. stearothermophilus suppressor tRNA (Tyr) is not recognized at all by aaRS such as TyrRS within cells, it is more preferably to also induce expression of suppressor tRNA as in the present example.

Reference Example

Construction of TyrRS Gene and Reporter

Gene

An FLAG tag (DYKDDDDK) was added to the C terminals of mutant TyrRS (V37C195) gene, ras gene and epithelial growth factor receptor reporter gene by amplifying these genes with suitable PCR primers. The PCR products were respectively cloned to vector pcDNA3.1/Zeo(+) (Invitrogen) in order to express them in mammalian cells. With respect to TyrRS (V37C195), the PCR product was also cloned to vector pcDNA4/TO (Invitrogen) to produce plasmid pRYSM1 for tetracycline-controlled expression. Site-directed mutagenesis of the ras gene was carried out by PCR using a mutation-inducing primer. Similarly, the tyrosine codon at position 1068 of epithelial growth factor receptor was mutated to an amber codon. The first methionine residue of green fluorescent protein (cyanofluorescent mutation) (Clontech) was substituted with a short peptide encoded by:

(SEQ. ID NO. 19)
ATGGGAACTAGTCCA<u>TAG</u>TGGTGGAATTCTGCAGATATCCAGCACAGTGG

CGGCCGCCGGTC (amber codon is underlined)

and a FLAG tag was added to the C terminal. The resulting gene was cloned to vector pcDNA3.1(Zeo(+). The sequence of the constructed gene was confirmed using the ABI Prism 377 DNA Sequencer (Applied Biosystems).

Transfection was carried out in accordance with the LipofectAMINE 2000 (Gibco BRL) method using 0.5 to 2 μg of DNA for each of the reporter gene expression vectors, suppressor tRNA expression vectors and E. coli TyrRS expression vectors. Opti-MEM 1 (Gibco BRL) was used for the medium. Cell extracts were prepared 24 hours after transfection and applied to SDS-PAGE followed by western blotting using anti-FLAG2 antibody (Sigma) and the ECL+Immunodetection System (Amersham Pharmacia Biotech). Band intensity was measured using the LAS-1000 Plus Image Analyzer (Fuji Film) (FIGS. 4A and 4B).

Figure 4A:
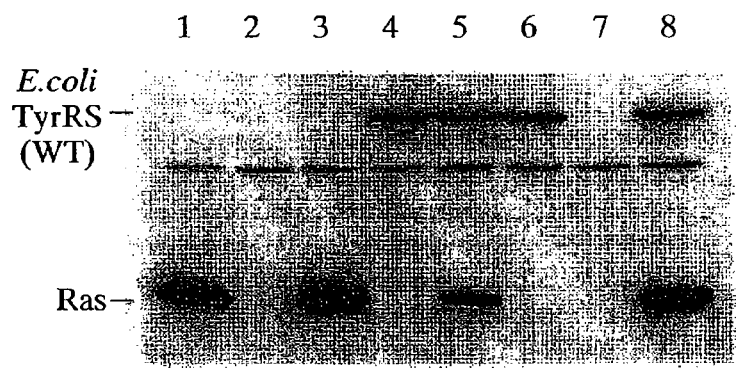
FIGS. 4A and 4B are photographs of the gels obtained from western blotting using anti-FLAG antibody for detecting an amber suppression in CHO cells.
Figure 4B:
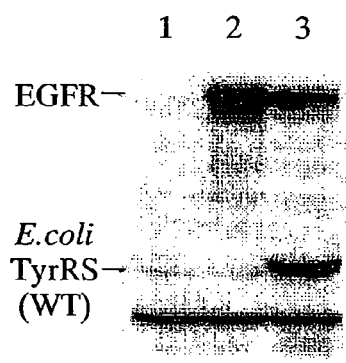

FIGS. 4A and 4B are photographs of the gel of the western blots obtained using anti-FLAG antibody in order to detect amber suppression of CHO cells.

In FIG. 4A, FLAG tags are respectively added to the wild type ras gene (Lane 1) and ras(Am) gene (Lanes 2-8), and these genes were introduced into the CHO cells. Human suppressor tRNA$^{Tyr}$ (Lane 3) or E. coli TyrRS and E. coli suppressor tRNA$^{Tyr}$ (Lane 4) were expressed in the CHO cells. B. stearothermophilus suppressor tRNA$^{Tyr}$ was expressed in the CHO cells together with E. coli TyrRS (Lanes 5 and 8) or in the absence of enzyme (Lane 7), and even E. coli TyrRS alone was expressed in the CHO cells (Lane 6). B. stearothermophilus suppressor tRNA$^{Tyr}$ was expressed from a plasmid having a single copy of the gene for this tRNA (Lanes 5 and 7) and from a plasmid having nine copies of the gene (Lane 8). Lane 1 contained 2.5 μg of cell extract, while lanes 2 to 8 contained four times that amount of cell extract.

In FIG. 4B, genes containing the amber codon at position 1068 (Lanes 1-3) as well as wild type EGFR gene (Lane 2) and epithelial growth factor receptor (EGFR) gene to which FLAG tags were respectively added were introduced into CHO cells. The B. stearothermophilus suppressor tRNA$^{Tyr}$ and E. coli TyrRS pair was expressed in the cells (Lane 3). The weak bands that migrated at the level of E. coli TyrRS in lanes 1 and 2 correspond to endogenous proteins that reacted to anti-FLAG antibody.

As shown in FIG. 4A, the co-expression of B. stearothermophilus suppressor tRNA and E. coli TyrRS was found to cause suppression of amber mutation in ras(Am) at an efficiency of 15% (FIG. 4A, Lane 5). This suppression did not occur in the absence of this tRNA (Lane 6) or enzyme (Lane 7). The need for E. coli TyrRS for suppression indicates that B. stearothermophilus suppressor tRNA$^{Tyr}$ is not aminoacylated by endogenous aaRS in cells. On the other hand, the expression of E. coli TyrRS from a transiently introduced plasmid itself hardly affect the growth rate of CHO cells.

The suppression efficiency of the tRNA$^{Tyr}$-TyrRS pair was considerably lower than the efficiency of human suppressor tRNA$^{Tyr}$ or other suppressor tRNAs that act in mammalian cells (20 to 40%). Since suppression efficiency was thought to be improved by increasing the copy number of suppressor tRNA gene, a plasmid was constructed that had nine copies of B. stearothermophilus suppressor tRNA$^{Tyr}$ gene, and this plasmid was introduced into CHO cells along with a plasmid having E. coli TyrRS gene. As a result, suppression efficiency was improved to 24% in this manner (FIG. 4A, Lane 8). This value is comparable to that of human suppressor tRNA$^{Tyr}$. This plasmid was subsequently used to express B. stearothermophilus suppressor tRNA$^{Tyr}$.

The pair consisting of B. stearothermophilus suppressor tRNA$^{Tyr}$ and E. coli TyrRS caused suppression of amber mutation in human embryonic kidney cell line 293 at the same efficiency as that in CHO cells. Moreover, amber mutation of epithelial growth factor receptor gene was suppressed at an efficiency of 20% (FIG. 4B), while amber mutation in Aequorea victoria green fluorescent protein gene was suppressed with the same efficiency.

These genes and ras(Am) gene have different codons surrounding the amber codon.

Comparative Example

Need for Expression of Prokaryotic tRNA$^{Tyr}$-TyrRS Pair for Amber Suppression in Mammalian Cells Expression of tRNA in eukaryotes requires two internal promoters (boxes A and B) within an RNA coding sequence. Since E. coli tRNA$^{Tyr}$ only contains box B, box A was created by substituting U9 and C10 with A and G, respectively. As a result, the resulting mismatch base pair, G10-G25, was corrected by substituting G25 with C. (to be referred to as tRNA$^{Tyr}$ (A9G10C25). Positions 9, 10 and 25 of E. coli tRNA$^{Tyr}$ are involved in three-dimensional interaction and support an L-shaped structure.

The sequence of tRNA$^{Tyr}$ (A9G10C25) having a CUA anticodon was coupled to the 5'-flanking sequence of human tRNA$^{Tyr}$ gene. Human suppressor tRNA$^{Tyr}$ gene was constructed in the same manner as the control of amber suppression. In order to analyze amber suppression, the tyrosine codon at position 32 in a synthetic ras gene truncated from the wild type c-Ha-Ras was mutated to an amber codon. In order to detect expression, a FLAG peptide tag was added to the C-terminals of the ras genes, ras(WT) and its amber mutant ras(Am), and to the C-terminal of E. coli TyrRS.

These ras gene were introduced into CHO cells, and their products were detected by western blotting of cell extracts using anti-FLAG antibody (FIG. 4A). Although expression of ras(WT) gene was detected in the absence of suppressor tRNA (Lane 1), expression of ras(Am) was not detected (Lane 2). This indicates that intrinsic suppressor activity is lacking in the cells. Human suppressor tRNA$^{Tyr}$ caused suppression of amber mutation in ras(Am) at an efficiency of 26% as measured on the basis of band intensity (Lane 3). On the other hand, *E. coli* tRNA$^{Tyr}$ (A9G10C25), which has a CUA anticodon, fail to cause suppression together with wild type TyrRS from *E. coli* (Lane 4). Next, we investigated another *E. coli* suppressor tRNA$^{Tyr}$ mutant using another nucleotide set capable of forming box A (G9G10C25). This tRNA was also unable to cause suppression. In this manner, the formation of box A in *E. coli* suppressor tRNA$^{Tyr}$ impaired its activity. This is probably because *E. coli* tRNA$^{Tyr}$ with box A fail to maintain the three-dimensional structure resulting in impairments of tRNA maturation or aminoacylation.

INDUSTRIAL APPLICABILITY

According to the expression method included in the present invention, non-naturally-occurring amino acids can be incorporated into a desired protein in response to nonsense codons, in the animal cells expressing the aforementioned mutant of *E. coli* TyrRS, the aforementioned suppressor tRNA derived from eubacterias, such as *Bacillus, Mycoplasma*, or *Staphylococcus*, and the gene coding for the desired protein with nonsense codons at desired positions. The non-naturally-occurring amino acids are taken up from the growth medium by the cells.

Previously, only *E. coli* cells were available for producing alloproteins, the proteins with non-naturally-occurring amino acids at desired positions. The present invention has enabled the production of such proteins in animal cells. Animal cells are better systems than *E. coli* cells for preparing the proteins from animals, including the human being, and would thus be useful for preparing alloproteins that are difficult to prepare with *E. coli* cells.

There are various applications for alloproteins. By the incorporation of 3-iodotyrosine or 4-iodo-L-phenylalanine, proteins can contain the heavy atom useful for X-ray crystallography or can be labeled with radioactive iodine atoms. In particular, iodine atoms would facilitate the functional and structural analyses of the proteins with iodine atoms, because this atom gives a characteristic signal for NMR spectroscopy.

Incorporation of O-methyltyrosine would also facilitate NMR analyses, because desired positions in a protein can be labeled with the stable isotope of carbon in the methyl group.

Incorporation of the non-naturally-occurring amino acids with acetyl groups, such as 4-acetylphnylalanine, would enable artificial modifications of proteins by chemical conjugation between the acetyl group, an reactive group, introduced into proteins and a variety of chemical compounds with desired properties and structure.

It has been reported that 4-benzoyl-L-phenylalanine and 4-azide-L-phenylalanine form a covalent bond with molecules in a close proximity upon exposure to the light with a certain wavelength (refer to, for example, J. Chin et al., Chem. Bio. Chem. 11, 1135-1137 (2002)). Thus, it si possible to detect unknown cellular targets that interact with the protein of interest, by incorporating these amino acids into this protein.

Moreover, some proteins with non-naturally-occurring amino acids possibly exhibit novel physiological properties to be subjected to the development of new drugs or drug-delivery systems.

Iodotyrosine-containing proteins would be useful in the study of cell signaling for the following two reasons. First, some tyrosine kinases (enzymes that phosphorylate tyrosine residues in cellular proteins) could phosphorylate iodotyrosine residues, and the other could not. The substrate specificities of these kinases could be engineered by utilizing the structural knowledge on these enzymes; the kinases capable of phosphorylating iodotyrosines could be engineered not to be capable, while the others not capable could similarly be engineered to be active with iodotyrosines. By site-specific incorporation of iodotyrosine into proteins, together with the introduction into cells of the kinase mutants thus engineered, it could be determine which kinase is involved in the phosphorylation on the tyrosine residue of interest.

Second, phosphorylated iodotyrosines are resistant, to some extent, to phosphatases, which remove the phosphoryl group from the phosphorylated tyrosine residues are thus involved, together with kinases, in the regular system based on protein phosphorylation. Proteins with phosphorylated iodotyrosines could keep its activity based on this phosphorylation for a longer time as compared with proteins with phosphorylated tyrosines, because of the resistant of iodotyrosine to phosphatases. Thus, the effects of the prolonged activity of a protein on cellular activities could be analyzed to elucidate the function ad role of this protein in the cell.

In addition, the systems expressing for suppressor tRNA in animal cells, included in the present invention, achieve nonsense suppression in these cells, and thus have a potential utility in the gene therapy of disease involved in nonsense mutations.

---

What is claimed is:

1. A DNA having a sequence selected from the group consisting of SEQ ID NO: 1, SEQ ID NO: 30, SEQ ID NO: 31 and SEQ ID NO: 32.

2. An expression vector capable of being expressed from a control sequence recognized in animal cells comprising a sequence selected from the group consisting of SEQ ID NO:1, SEQ ID NO:30, SEQ ID NO:31 and SEQ ID NO:32.

3. The expression vector according to claim 2 that carries nine copies of DNAs having the sequence of SEQ ID NO: 1.

* * * * *

UNITED STATES PATENT AND TRADEMARK OFFICE
CERTIFICATE OF CORRECTION

PATENT NO. : 7,666,640 B2
APPLICATION NO. : 12/488136
DATED : February 23, 2010
INVENTOR(S) : Shigeyuki Yokoyama et al.

It is certified that error appears in the above-identified patent and that said Letters Patent is hereby corrected as shown below:

On the Title Page Item (73) Assignees should read: Riken (JP);
Japan Science and Technology Agency (JP)

Signed and Sealed this

Thirteenth Day of April, 2010

David J. Kappos
*Director of the United States Patent and Trademark Office*